US 9,272,142 B2

(12) United States Patent
Botros et al.

(10) Patent No.: US 9,272,142 B2
(45) Date of Patent: Mar. 1, 2016

(54) SYSTEMS AND METHODS FOR USING A SIMPLIFIED USER INTERFACE FOR HEARING PROSTHESIS FITTING

(75) Inventors: Andrew Botros, Lane Cove (AU); Bastiaan Van Dijk, Mechelen (BE); Rami Banna, Lane Cove (AU)

(73) Assignee: Cochlear Limited, Macquarie University, NSW (AU)

( * ) Notice: Subject to any disclaimer, the term of this patent is extended or adjusted under 35 U.S.C. 154(b) by 440 days.

(21) Appl. No.: 13/016,315

(22) Filed: Jan. 28, 2011

(65) Prior Publication Data

US 2012/0197065 A1 Aug. 2, 2012

(51) Int. Cl.
*A61N 1/36* (2006.01)
*A61N 1/372* (2006.01)
*H04R 25/00* (2006.01)

(52) U.S. Cl.
CPC ........ *A61N 1/36032* (2013.01); *A61N 1/37247* (2013.01); *H04R 25/70* (2013.01)

(58) Field of Classification Search
CPC ........... A61N 1/08; A61N 1/00; H04R 25/00; A61F 2/18
USPC ..................... 600/25, 558; 381/23.1, 68, 312; 607/55–57, 137; 623/10
See application file for complete search history.

(56) References Cited

U.S. PATENT DOCUMENTS

| 4,532,930 | A | | 8/1985 | Crosby |
|---|---|---|---|---|
| 5,607,455 | A | * | 3/1997 | Armstrong ........................ 607/8 |
| 6,157,861 | A | | 12/2000 | Faltys et al. |
| 6,289,247 | B1 | | 9/2001 | Faltys et al. |
| 6,537,200 | B2 | | 3/2003 | Leysieffer |
| 6,565,503 | B2 | | 5/2003 | Leysieffer |
| 6,575,894 | B2 | | 6/2003 | Leysieffer |
| 6,697,674 | B2 | | 2/2004 | Leysieffer |
| 7,167,754 | B1 | | 1/2007 | Peeters et al. |
| 2004/0082980 | A1 | | 4/2004 | Mouine et al. |
| 2005/0129262 | A1 | | 6/2005 | Dillon et al. |
| 2006/0235332 | A1 | * | 10/2006 | Smoorenburg ............... 600/559 |
| 2008/0187146 | A1 | * | 8/2008 | Yanz et al. ...................... 381/60 |
| 2008/0300653 | A1 | | 12/2008 | Svirsky |
| 2008/0319508 | A1 | | 12/2008 | Botros |
| 2009/0043359 | A1 | * | 2/2009 | Smoorenburg ................. 607/57 |

(Continued)

OTHER PUBLICATIONS

International Search Report for PCT Application No. PCT/IB2012/000087 mailed Sep. 19, 2012 (7 pages).

(Continued)

*Primary Examiner* — Christine H Matthews

(57) ABSTRACT

The present application discloses systems and methods for displaying and operating a user interface having one or more channel group controllers corresponding to one or more groups of hearing prosthesis channels. The hearing prosthesis may be configured to generate a plurality of signals via a plurality of channels based on a channel profile. The channel profile may define at least one intensity level for each channel. In operation, the user interface may be configured to instruct the hearing prosthesis to change the channel profile of the plurality of channels in response to receiving an input via one of the channel group controllers. The user interface may be used to fit a hearing prosthesis to a recipient. In one embodiment, an initial channel profile may be automatically determined, and the prosthesis channel profile may be adjusted by changing a representative intensity level corresponding to the channel profile.

28 Claims, 10 Drawing Sheets

(56) References Cited

U.S. PATENT DOCUMENTS

2010/0268302 A1 10/2010 Botros
2011/0299709 A1* 12/2011 Anderson et al. ............. 381/315

OTHER PUBLICATIONS

European Search Report for European Patent Application 12739114.2 dated Aug. 12, 2014.

English translation of Second Office Action in counterpart Chinese Application No. 201280006792.2, dated Oct. 10, 2015, 3 pages.
First Examination Report in counterpart Australian Application No. 2012210291, issued Aug. 13, 2015, 3 pages.
Examination Report in counterpart European Application No. 12 739 114.2, dated Oct. 13, 2015, 4 pages.

\* cited by examiner

SYSTEMS AND METHODS FOR USING A SIMPLIFIED USER INTERFACE FOR HEARING PROSTHESIS FITTING

BACKGROUND

Various types of hearing prostheses may provide persons with different types of hearing loss with the ability to perceive sound. Hearing loss may be conductive, sensorial, or some combination of both conductive and sensorial hearing loss. Conductive hearing loss typically results from a dysfunction in any of the mechanisms that ordinarily conduct sound waves through the outer ear, the eardrum, or the bones of the middle ear. Sensorial hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing devices, such as acoustic hearing aids, bone anchored hearing aids, direct acoustic cochlear stimulation devices, or auditory brain stem implants. An acoustic hearing aid typically includes a small microphone to detect sound, an amplifier to amplify certain portions of the detected sound, and a small speaker to transmit the amplified sounds into the person's ear. A bone anchored hearing aid typically utilizes a surgically-implanted mechanism to transmit sound via direct bone vibrations. In operation, vibrations corresponding to sound waves are applied directly to a person's bone to cause vibrations in the person's inner ear, bypassing the person's auditory canal and middle ear. A direct acoustic cochlear stimulation device typically utilizes a surgically-implanted mechanism to transmit sound via vibrations corresponding to sound waves to generate fluid motion in a person's inner ear.

Persons with certain forms of sensorial hearing loss may benefit from cochlear implants. Cochlear implants may provide a person having sensorineural hearing loss with the ability to perceive sound by stimulating the person's auditory nerve via an array of electrodes implanted in the person's cochlea. An external component of the cochlear implant detects sound waves, which are converted into a series of electrical stimulation signals delivered to the implant recipient's auditory nerve via the array of electrodes. Stimulating the auditory nerve in this manner may enable the cochlear implant recipient's brain to perceive a hearing sensation that is similar to the natural hearing sensation delivered to the auditory nerve.

The effectiveness of the above-described prostheses depend not only on the design of the prosthesis itself but also on how well the prosthesis is configured for or "fitted" to a prosthesis recipient. The fitting of the prosthesis, sometimes also referred to as "programming" or "mapping," creates a set of configuration settings and other data that defines the specific characteristics of the signals (acoustic, mechanical, or electrical) delivered to the relevant portions of the person's outer ear, middle ear, inner ear, or auditory nerve. This configuration information is sometimes referred to as the recipient's "program" or "MAP."

Typically, a hearing prostheses may be fitted to a prosthesis recipient by an audiologist or other similarly trained professional who may use a sophisticated fitting procedure to individually set multiple levels for multiple channels of the hearing prosthesis. Sophisticated fitting programs may be advantageous in some situations because they may give an audiologist or other similarly trained professional a great deal of control and flexibility over the hearing prosthesis fitting parameters.

SUMMARY

The present application discloses systems and methods for displaying and/or using a simplified user interface to configure a hearing prosthesis. In some embodiments, the hearing prosthesis may be a cochlear implant, an acoustic hearing aid, a bone anchored hearing aid, a direct acoustic cochlear stimulation device, or an auditory brain stem implant. In some embodiments, the simplified user interface may include a first channel group controller corresponding to a first group of channels of the hearing prosthesis. The hearing prosthesis may be configured to generate a first set of signals via the first group of channels based on a first channel profile. The signals may correspond to acoustic signals, mechanical vibration signals, or electrical stimulation signals.

In some embodiments, the first channel profile may define at least one intensity level for each channel in the first group of channels. In some embodiments, the first channel group controller may be displayed on a first user interface as any one of a rotator knob, slider bar, an up/down button, or any other similarly intuitive controller icon. In some embodiments, the first channel group controller may be a physical knob, a physical slider bar, a physical up/down button, or any other similarly intuitive controller.

The simplified user interface in some embodiments may be configured to receive an input via the first channel group controller. The simplified user interface may be further configured to change the first channel profile of the first group of channels in response to receiving the input via the first channel group controller. In some embodiments, the simplified user interface may also be configured to instruct the hearing prosthesis to change one or more of its configuration settings based on the change to the first channel profile.

In some embodiments, a first representative intensity level corresponding to the first group of channels may be associated with the first channel profile. In these embodiments, the simplified user interface may be configured to display a unit value corresponding to the first representative intensity level. In some embodiments, the first representative intensity level may be one of a maximum, minimum, mean, or median value of the intensity levels of the channels of the first group of stimulation channels.

In some embodiments, the hearing prosthesis may be further configured to generate a second set of signals via a second group of channels based on a second channel profile. In these embodiments, the simplified user interface may further include of a second channel group controller corresponding to the second group of channels. In these embodiments, the simplified user interface may be further configured to receive an input via the second channel group controller and to change the second channel profile of the second group of channels in response to receiving the input via the second channel group controller. In some embodiments, the simplified user interface may also be configured to instruct the hearing prosthesis to change one or more of its configuration settings based on the change to the second channel profile.

Some embodiments of the disclosed systems and methods may include automatically determining a channel profile (such as the first channel profile) corresponding to a plurality of channels of the hearing prosthesis. In some embodiments, the automatically-determined channel profile may be based on an estimated equal loudness contour for a plurality of channels of the hearing prosthesis. The estimated equal loudness contour for the plurality of channels may in some embodiments be based on an analysis of a measured neural response to at least one signal.

Some embodiments may also include automatically determining an amplitude and/or a pulse width setting for one or more signals based on an estimated power consumption. The power consumption estimate may be based on an intensity level for a channel corresponding to the signal. Some embodiments may also include testing one or more channels of the hearing prosthesis and disabling any malfunctioning channels.

In some embodiments, the simplified user interface may be configured to receive a command to increase the representative intensity level of the channel profile by one unit value. In these embodiments, the simplified user interface may also be configured to instruct the hearing prosthesis to generate at least one signal based on the increased channel profile.

Limiting the increase of the representative intensity level to a single unit value at a time may operate as a safety function to prevent the channel profile from being increased too rapidly so that the signals generated by the hearing prosthesis do not become uncomfortably loud unexpectedly. Similarly, by instructing the hearing prosthesis to generate at least one signal based on the increased channel profile, the prosthesis recipient can listen to sound at the increased channel profile before choosing to further increment the representative intensity level.

In some of the disclosed embodiments, changes made to the channel profile of the hearing prosthesis via the simplified user interface may be viewable and/or modifiable via a complex user interface and vice versa. The complex user interface may include a plurality of individual channel controllers, where each channel controller is configured to control at least one intensity level for a single corresponding channel of the plurality of channels of the hearing prosthesis.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Certain aspects of the disclosed systems and methods are described herein with reference to cochlear implants. However, the disclosed systems and methods are not so limited. Many aspects of the disclosed systems and methods may be equally applicable to other types of hearing prostheses, such as, for example, acoustic hearing aids, bone anchored hearing aids, direct acoustic cochlear stimulation devices, auditory brain stem implants, or any other type of hearing prosthesis that may be configured to generate acoustic signals, mechanical vibration signals, or electrical signals at configurable frequencies and intensities.

1. Cochlear Implant Overview

Figure 1A:
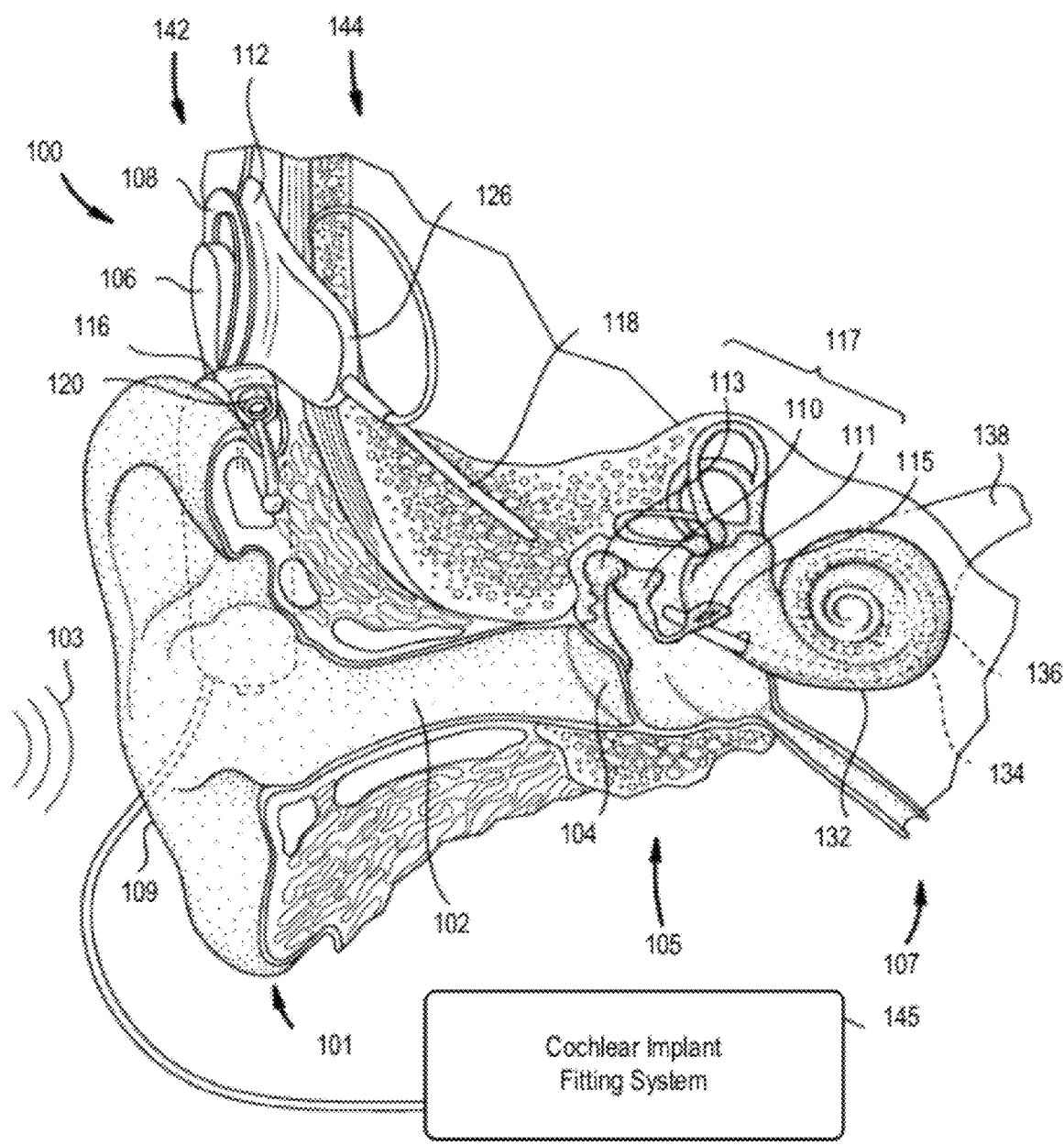
FIG. 1A shows one example embodiment of a cochlear implant that may be implanted into an implant recipient.

FIG. 1A shows an example of a cochlear implant 100 implanted in a cochlear implant recipient according to some embodiments of the disclosed systems and methods. The relevant components of the recipient's outer ear 101, middle ear 105, and inner ear 107 are described herein, followed by a description of the cochlear implant 100.

An acoustic pressure or sound wave 103 is collected by the auricle 109 and channeled into and through the ear canal 102. The tympanic membrane 104 is located at the distal end of the ear canal 102. The tympanic membrane 104 vibrates in response to the acoustic wave 103.

The vibration of the tympanic membrane 104 is coupled to the oval window or fenestra ovalis 115 through three bones of the middle ear 105, collectively referred to as the ossicles 117, and including the malleus 113, the incus 110, and the stapes 111. For persons without particular hearing impairments, bones 113, 110 and 111 of the middle ear 105 serve to filter and amplify the acoustic wave 103, causing the oval window 115 to articulate and/or vibrate. The vibration of the oval window 115 causes waves of fluid motion within the cochlea 132. This fluid motion within the cochlea 132, in turn, activates tiny hair cells (not shown) that line the inside of the cochlea 132. Activation of the hair cells inside the cochlea 132 causes nerve impulses to be transferred through the spiral ganglion cells (not shown) and the auditory nerve 138 to the brain (not shown), where the nerve impulses may be perceived as sound. But for persons with sensorial hearing loss, a cochlear implant may be used to create and apply electrical stimulation signals that may be detected by a person's auditory nerve and perceived as sound.

The cochlear implant 100 may include an external component assembly 142 that is directly or indirectly attached to the body of the recipient, and an internal component assembly 144 that is temporarily or permanently implanted in the recipient.

The external assembly 142 may include a sound processing unit 116 and an external transmitter unit 106. The sound processing unit 116 may include a digital signal processor (DSP), a power source to power the cochlear implant 100, and a sound transducer 120. The sound transducer 120 may be configured to detect sound and to generate an audio signal, typically an analog audio signal, representative of the detected sound. In the example embodiment shown in FIG. 1A, the sound transducer 120 is a microphone. In alternative embodiments, the sound transducer 120 may comprise, for example, more than one microphone, one or more telecoil induction pickup coils, or other devices now or later developed that may detect sound and generate electrical signals representative of detected sound. In some embodiments, the sound transducer 120 may not be integrated into the sound processing unit 116, but rather could be a separate component of the external component assembly 142.

The external transmitter unit 106 may include an external coil 108 of a transcutaneous energy transfer system along with the associated circuitry to drive the coil. The external transmitter unit 106 may also preferably include a magnet (not shown) secured directly or indirectly to the external coil 108.

The sound processing unit 116 may be configured to process the output of the microphone 120 that is positioned, in the depicted embodiment, near the auricle 109 of the recipient. The sound processing unit 116 may be configured to generate coded signals, referred to herein as stimulation signals, which can be provided to the external transmitter unit 106 via a cable (not shown). The sound processing unit 116 shown in this example embodiment is designed to fit behind the auricle 109. Alternative versions may be worn on the body, or it may be possible to provide a fully implantable system that incorporates the sound processing unit into the internal component assembly 144.

The internal component assembly 144 may include an internal receiver unit 112, a stimulator unit 126 and an electrode assembly 118. The internal receiver unit 112 and the stimulator unit 126 may be hermetically sealed within a biocompatible housing.

The internal receiver unit 112 may include an internal coil (not shown) of the noted transcutaneous transfer system, along with the associated circuitry. The implanted internal receiver unit 112 may be positioned in a recess of the temporal bone adjacent to the outer ear 101 of the recipient, as shown in FIG. 1A. The external coil 108 may be held in place and aligned with the implanted internal coil via the noted magnets. In one embodiment, the external coil 108 may be configured to transmit electrical signals to the internal coil via a radio frequency (RF) link.

The electrode assembly 118 may be designed to extend from the stimulator unit 126 to the cochlea 132 and to terminate in an array 134 of electrodes 136. Stimulation signals generated by the stimulator unit 126 are applied by the electrodes 136 to the cochlea 132, thereby stimulating the auditory nerve 138.

Further details of the above and other examples of cochlear implants that may be implemented in conjunction with embodiments of the disclosed systems and methods include, but are not limited to, those systems described in U.S. Pat. Nos. 4,532,930, 6,537,200, 6,565,503, 6,575,894 and 6,697,674, which are hereby incorporated by reference herein in their entireties.

As shown in FIG. 1A, the cochlear implant 100 may be further configured to interoperate with a cochlear implant fitting system 145. The hearing implant fitting system 145 may be implemented with a computing device, such as a personal computer, workstation, handheld computing device, or the like. The fitting process is described in greater detail below with reference to an exemplary fitting environment illustrated in FIG. 1B.

2. Fitting System Overview

The effectiveness of the cochlear implant 100 or any other hearing prosthesis depends not only on the device itself but also on how well the device is configured for or "fitted" to the recipient. The fitting of the cochlear implant, sometimes also referred to as "programming" or "mapping," creates a set of configuration settings and other data that defines the specific characteristics of the stimulation signals delivered to the electrodes 136 of the implanted array 134. This configuration information is sometimes referred to as the recipient's "program" or "MAP."

Figure 1B:
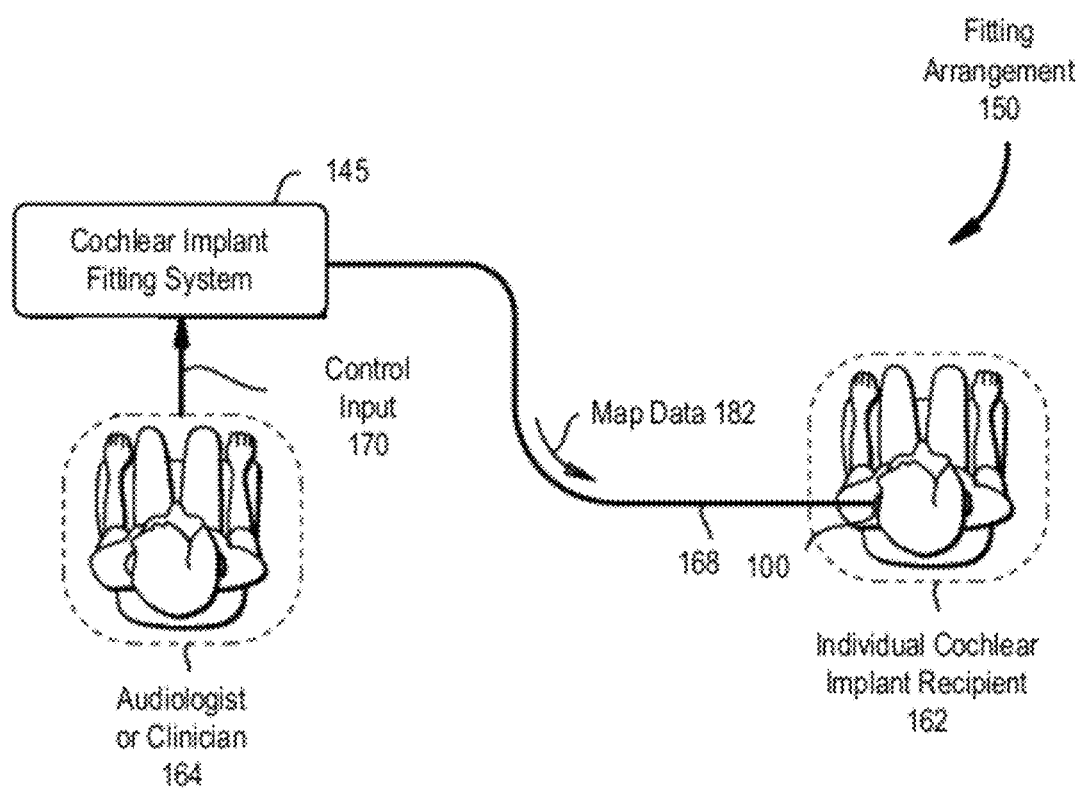
FIG. 1B shows an example of an audiologist or other similarly-trained clinician fitting a cochlear implant to an implant recipient according to some embodiments of the disclosed systems and methods.

FIG. 1B is a schematic diagram illustrating one example arrangement 150 where an audiologist or other clinician 164 may use the cochlear implant fitting system 145 to fit a cochlear implant 100 to a recipient 162 according to some embodiments of the disclosed systems and methods. The cochlear implant fitting system 145 may include interactive software and computer hardware and/or firmware configured to create a recipient-specific implant configuration, shown as "map data" 182 in FIG. 1B. The map data 182 may be stored on the fitting system 145, and it also may be downloaded to the memory of the sound processing unit 116 (FIG. 1A) of the cochlear implant 100. Other hearing prosthesis may be fitted to a recipient in a similar manner.

In the example shown in FIG. 1B, the sound processing unit 116 of the cochlear implant 100 may be communicatively coupled to the fitting system 145 to establish a data communication link 168 between the cochlear implant 100 and the fitting system 145. The fitting system 145 may thereafter be bi-directionally coupled to the cochlear implant 100 via the data communication link 168. Although the cochlear implant 100 and fitting system 145 are connected via a cable in FIG. 1B, any communications link now or later developed may be utilized to communicably couple these components, e.g., for example, a radio link or other communications link.

After the cochlear implant 100 has been implanted, specific map data 182 may be determined for the recipient. The particular details of the implemented fitting process may be specific to the recipient, cochlear implant manufacturer, cochlear implant device, etc. As a result, only selected example mapping data are described herein for clarity.

Typically, most cochlear implants may require at least two values to be set for each stimulation channel of the array 134 of electrodes 136 of the cochlear implant 100. A stimulation channel may generally include at least one active electrode and at least one reference electrode of the array 134 of electrodes 136. The typical values set for each stimulation channel are referred to as the threshold level (commonly referred to as the "THR" or "T-level"; "threshold level" herein) and the Maximum Comfortable Loudness level (commonly referred to as the Most Comfortable Loudness level, "C-level"; simply "comfort level" herein). Threshold levels and comfort levels may vary from recipient to recipient and from stimulation channel to stimulation channel. The threshold levels and the comfort levels determine in part how well the recipient hears and understands detected speech and/or sound. Other hearing prosthesis may have similar maximum and minimum signal intensity levels, such as, for example, maximum and minimum acoustic levels or maximum and minimum mechanical vibration levels.

The threshold level may correspond to the level where the recipient first identifies sound sensation. In general, the threshold level is the lowest intensity level of stimulation current that evokes the sensation of sound for a given stimulation channel. In a typical fitting scenario, the threshold level may often be determined for each stimulation channel by passing the recipient's hearing threshold twice using an ascending method and determining the level at which the recipient experiences sound by observing their response, such as, for example, indicating gestures in the case of adults, or observing behavioral reactions in the case of children.

The comfort level may set the maximum allowable stimulation level for each stimulation channel. The comfort level may correspond to the maximum intensity level of stimulation current that feels comfortable to the recipient. In setting and establishing the comfort levels for each stimulation channel, it may be typical for an audiologist or clinician to instruct the recipient to indicate a level that is "as loud as would be comfortable for long periods" while slowly increasing the stimulation level for a particular stimulation channel. The comfort levels may generally affect how speech sounds to the recipient more than the threshold levels because most of the acoustic speech signal may generally be mapped onto approximately the top 20% of the threshold and comfort level range.

Although the terminology and abbreviations may be device-specific, the general purpose of setting each threshold and comfort level for each channel is to determine a recipient's dynamic range for each channel by defining the lowest intensity levels (threshold levels) and the highest acceptable intensity levels (comfort levels) for each channel.

3. Stimulation Signals

Figure 1C:
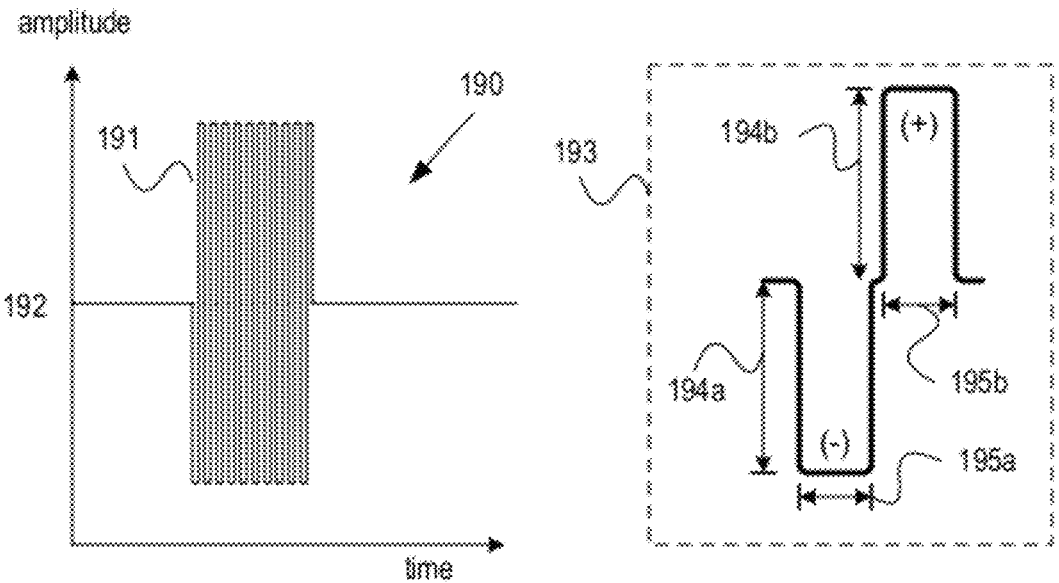
FIG. 1C shows an example of a stimulation signal that may be generated on a stimulation channel by a cochlear implant according to some embodiments of the disclosed systems and methods.

FIG. 1C shows a graph 190 of an example of an electrical stimulation signal 191 that may be generated by a cochlear implant on a particular stimulation channel according to some embodiments of the disclosed systems and methods. The graph 190 illustrated in FIG. 1C shows the stimulation signal amplitude versus time, where the stimulation signal's amplitude is shown on the vertical axis and time is shown on the horizontal axis. Trace 192 corresponds to one stimulation channel of the cochlear implant.

The stimulation signal 191 may include one or more current pulses. The stimulation signal 191 shown in FIG. 1C includes a group of substantially square wave pulses, but other types of waveforms could be used as well. An expanded view of one current pulse 193 of the stimulation signal 191 is shown in the inset. The current pulse 193 of the stimulation signal 191 shown here is a charge-balanced, biphasic current pulse having an amplitude and pulse width. In some embodiments, the biphasic current pulse may also have a phase gap between the positive and negative phases of the pulse. The amplitude $194a$ and pulse width $195a$ of the negative phase of the current pulse 193 are substantially the same as the amplitude $194b$ and pulse width $195b$ of the positive phase of the current pulse 193. As a result, the electrical stimulus delivered to a nerve in the positive phase of the current pulse may be substantially the same as the electrical stimulus delivered to the nerve in the negative phase of the current pulse so that substantially no net charge remains after the completion of an individual current pulse 193. The stimulation signal 191 may include multiple biphasic current pulses that may be similar to the biphasic current pulse 193.

In the biphasic current pulse 193 shown in FIG. 1C, the amplitude 194 may correspond to a level of electrical current delivered via the stimulation signal. In some embodiments, the current level may represent the amplitude of the biphasic current pulse in microamperes ($\mu A$), where a higher amplitude may correspond to a higher intensity signal and a lower amplitude may correspond to a lower intensity signal. In some embodiments, the amplitude range may be substantially from about 10 $\mu A$ to about 1.75 mA (or 1750 $\mu A$), but other ranges may be used in other embodiments. The pulse width 195 may correspond to the amount of time that the current is applied via the stimulation channel, expressed in microseconds ($\mu s$) per phase of the biphasic current pulse 193.

A charge per phase of the biphasic current pulse 193 may be calculated by multiplying the amplitude 194 of the biphasic current pulse 193 by the pulse width 195 of the biphasic current pulse 193. A biphasic current pulse with a higher charge per phase may cause the recipient to experience a louder sound sensation than a biphasic pulse with a lower charge per phase. Because the charge per phase is the product of the amplitude and pulse width, increasing either the amplitude or the pulse width of a biphasic current pulse of a stimulation signal may cause the recipient to experience a louder sound sensation, while decreasing either the amplitude or the pulse width of the biphasic current pulse of the stimulation signal may cause the recipient to experience a softer sound sensation.

4. User Interfaces for Hearing Prosthesis Configuration

Figure 2A:
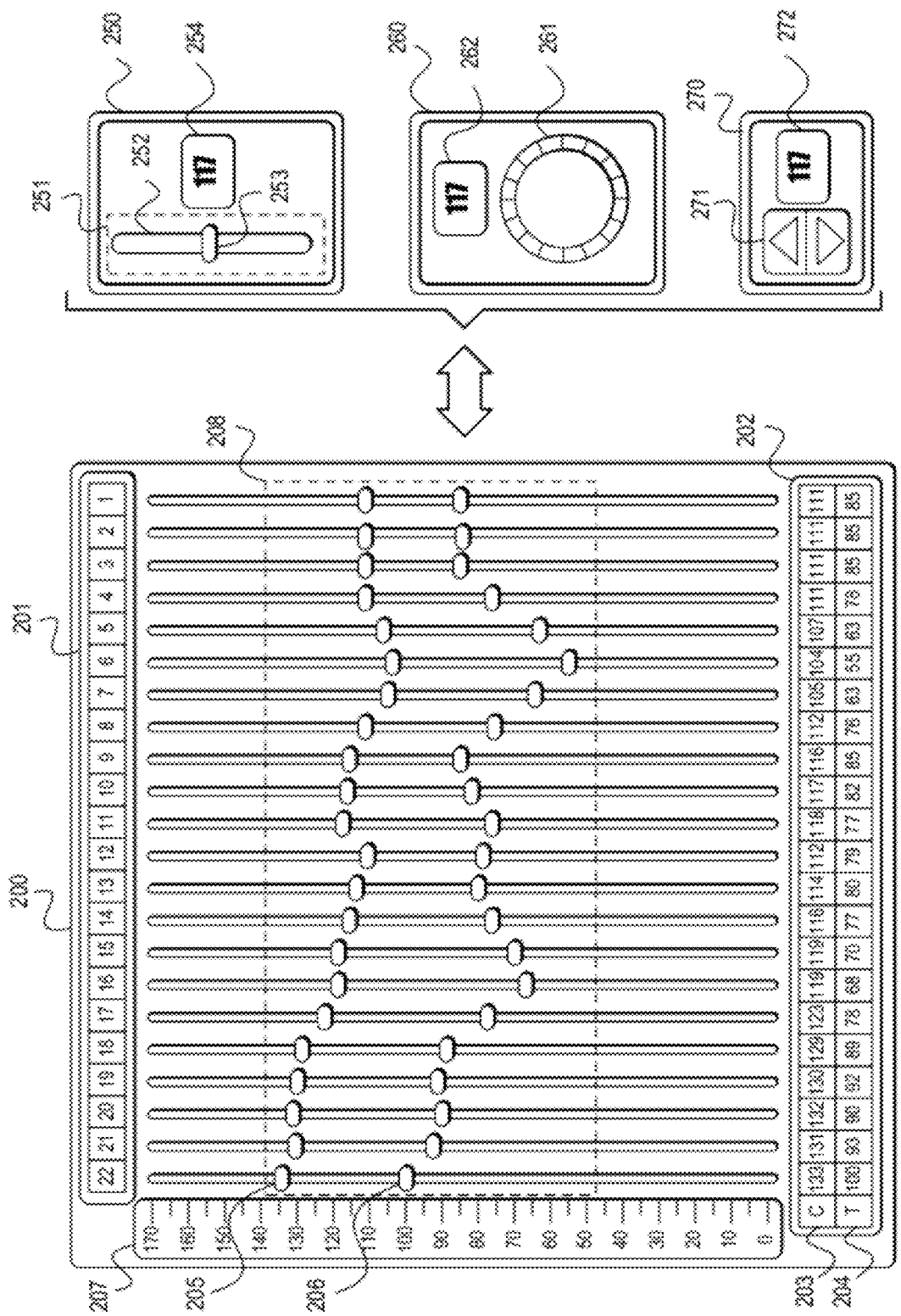
FIGS. 2A-C show examples of simplified and complex user interfaces configured to adjust the stimulation profile of a cochlear implant according to some embodiments of the disclosed systems and methods.
Figure 2B:
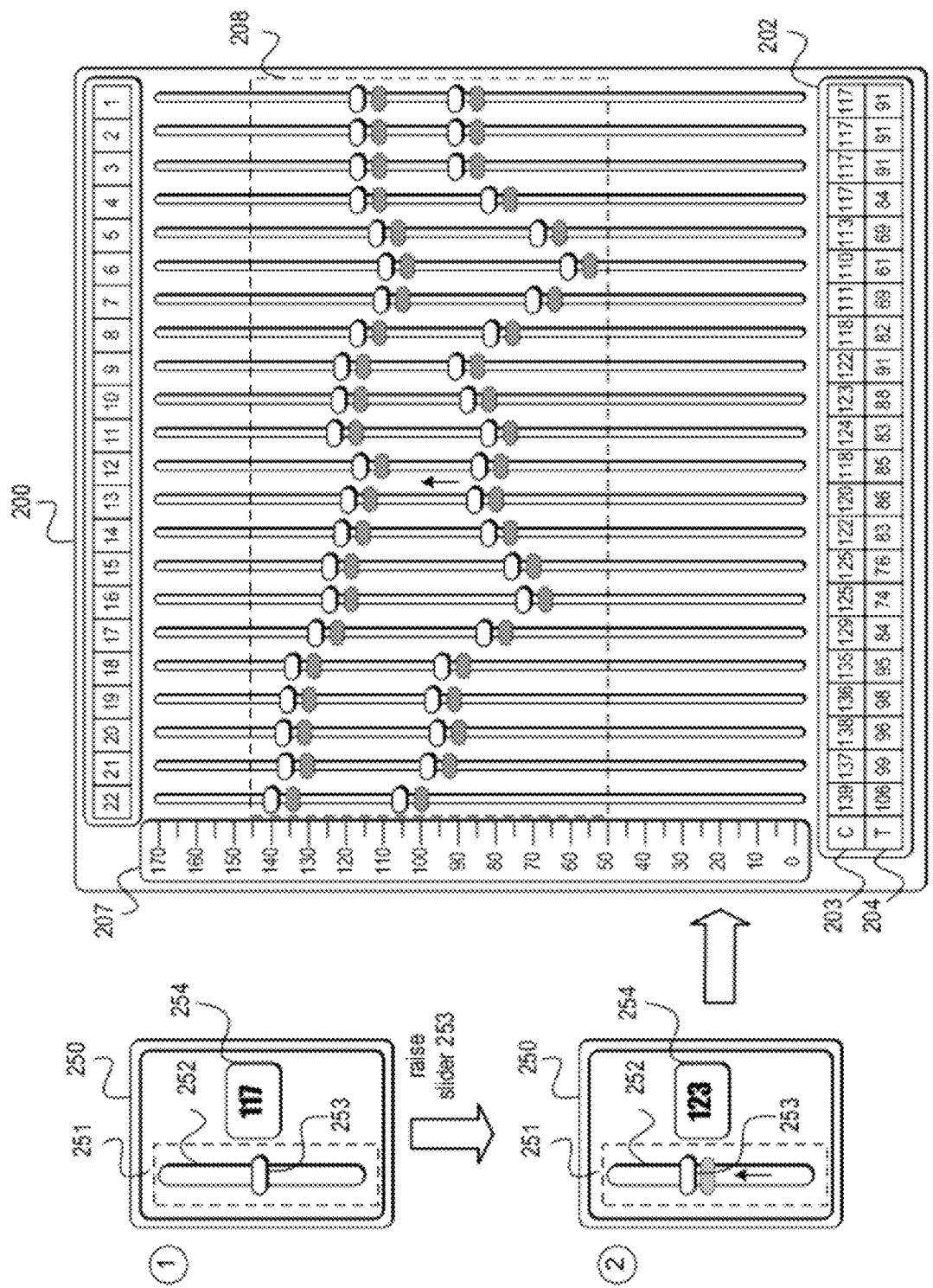
Figure 2C:
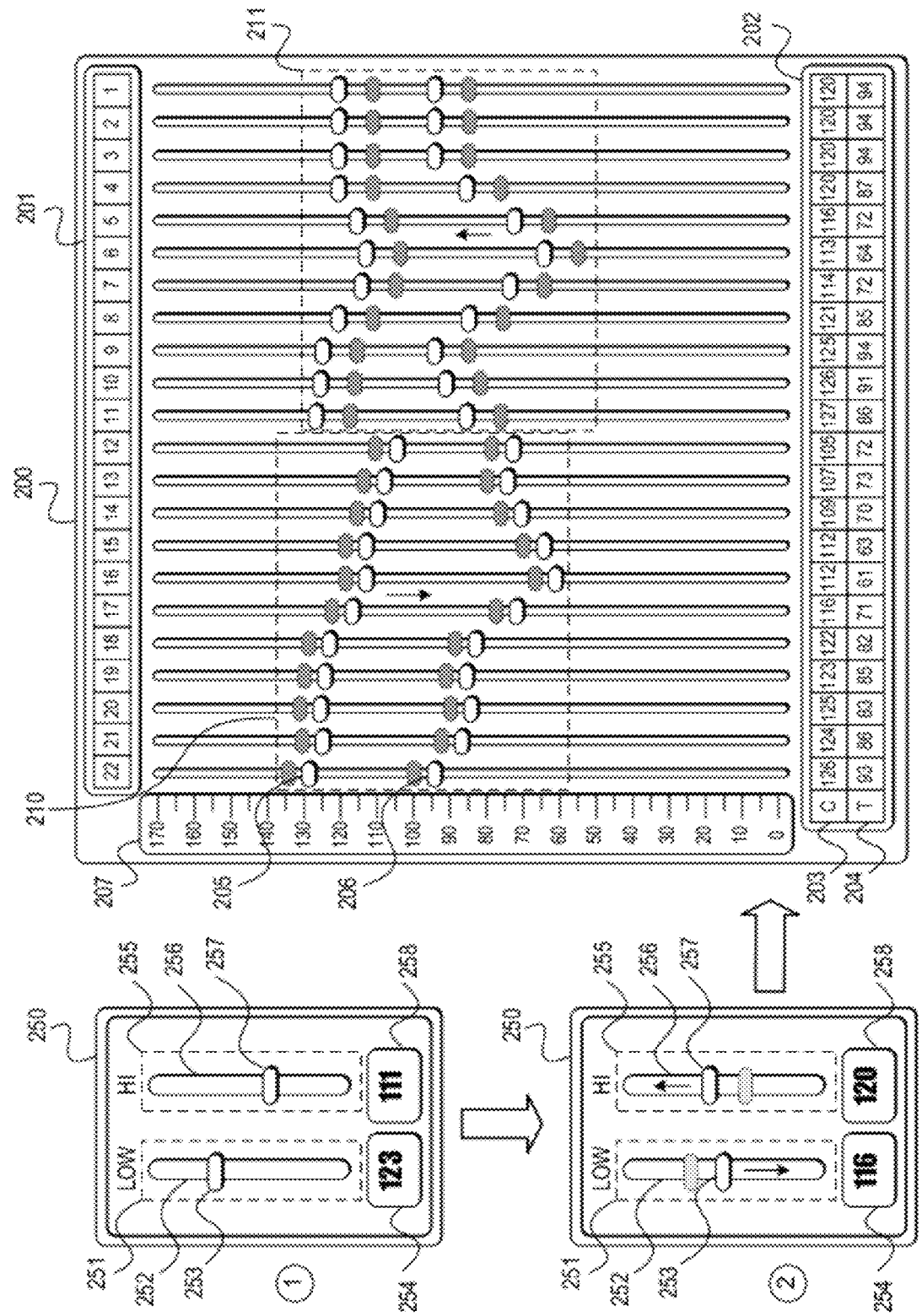

FIGS. 2A-C show examples of user interfaces configured to adjust settings of a hearing prosthesis according to some embodiments. FIG. 2A shows how a cochlear implant's stimulation profile may be represented in either a complex user interface 200 or a simplified user interface 250, 260, or 270, and FIGS. 2B-C show how changes made to a cochlear implant's stimulation profile via a simplified user interface 250 may be reflected in a complex user interface 200 and vice versa.

4.1 Complex User Interface

Complex user interface 200 shows an example of one type of user interface that an audiologist or other similarly trained professional may use to fit a cochlear implant or other hearing prosthesis to a recipient. In general, the complex user interface 200 may have an individual channel controller for each stimulation channel of the cochlear implant. The complex user interface 200 shown in FIGS. 2A-C is designed for use with a cochlear implant equipped with 22 stimulation channels. Similar user interfaces may be used with other cochlear implants having greater than or less than 22 stimulation channels. Likewise, user interfaces for use with other types of hearing prostheses may have greater than or less than 22 channels.

Box 201 across the top of the complex user interface 200 shows a channel number for each of the 22 stimulation channels of the cochlear implant. Box 202 across the bottom of the complex user interface 200 shows a set of comfort levels (C-levels) 203 and a set of threshold levels (T-levels) 204. The set of C-levels 203 includes a comfort level setting for each of the 22 channels of the cochlear implant. Similarly, the set of T-levels 204 includes a threshold level setting for each of the 22 channels of the cochlear implant.

In the complex user interface 200, the C-level and T-level for a particular stimulation channel are shown on a channel slider bar corresponding to that particular stimulation channel. For example, the C-level for stimulation channel 22 is set to a value of 133 and is indicated on the slider bar associated with channel 22 by slider 205. Similarly, the T-level for stimulation channel 22 is set to a value of 100 and is indicated on the slider bar associated with channel 22 by slider 206. The position of sliders 205 and 206 correspond to the numeric values shown on the axis 207 along the left side of the complex user interface 200. In this manner, the numeric values of the C-level and T-level for each stimulation channel shown in box 202 along the bottom of the complex user interface 200 correspond to the positions of the sliders on each corresponding channel bar.

In the embodiment shown in FIG. 2A, the set of C-level or T-level values for the set of stimulation channels 208 are referred to as the stimulation profile, or channel profile, for the set of stimulation channels 208. In other embodiments, a first stimulation profile may correspond to the stimulation levels of a first set of stimulation channels, and a second stimulation profile may correspond to the stimulation levels of a second set of stimulation channels, etc., as described in more detail herein. Trained professionals may typically set each C-level and each T-level of each of the 22 stimulation channels individually during the fitting process.

Because the complex user interface 200 may enable each C-level and each T-level of each of the 22 stimulation channels to be individually adjusted, the complex user interface 200 may provide a very high degree of flexibility in the fitting process to enable finely-tuned fitting of the implant to a particular recipient.

4.1 Simplified User Interfaces

FIG. 2A also shows an example of a simplified user interface 250 according to some embodiments. The simplified user interface 250 may include a channel group controller 251 corresponding to a group of channels of the hearing prosthesis. In the embodiment shown in FIG. 2A, the simplified user interface 250 includes a stimulation channel group controller 251 corresponding to a group of stimulation channels of the cochlear implant. The stimulation channel group controller 251 may include a slider bar 252 and a slider 253. The stimulation channel group controller 251 may be configured to adjust the stimulation levels (i.e., C-levels, T-levels, or other similar stimulation levels) of a group of stimulation channels of a cochlear implant.

In the embodiment shown in FIG. 2A, the stimulation channel group controller 251 corresponds to the set of stimulation channels 208 that includes all 22 stimulation channels of the cochlear implant. Thus, the simplified user interface 250 may be used to adjust the stimulation levels of all 22 stimulation channels of the cochlear implant by moving the slider 253 up or down along the slider bar 252. In other embodiments, a stimulation channel group controller may correspond to less than all the channels of a cochlear implant, as described in more detail herein.

The simplified user interface 250 may also have a representative stimulus level indicator 254 that is configured to display a representative stimulus level corresponding to the group of stimulation channels that may be controlled by the stimulation channel group controller 251. In the embodiment shown in FIG. 2A, the stimulation channel group controller 251 of the simplified user interface 250 corresponds to all 22 channels of the cochlear implant, and thus, the representative stimulus level displayed by the representative stimulus level indicator 254 corresponds to a representative stimulus level for all 22 channels of the cochlear implant. In other embodiments, the representative stimulus level indicator may correspond to less than all 22 channels of the cochlear implant.

In the embodiment shown in FIG. 2A, the representative stimulus level displayed in the representative stimulus level indicator 254 is equal to the mean stimulus level of the set of C-levels for all 22 channels of the cochlear implant. In other embodiments, the representative stimulus level may correspond to a maximum stimulus level of the stimulation channels, a minimum stimulus level of the stimulation channels, or a median stimulus level of the stimulation channels. In some embodiments, the representative stimulus level may correspond to some other numerical value that is based at least in part on a stimulation level of a stimulation channel in a particular group of two or more stimulation channels that may be controlled by a particular corresponding stimulation channel group controller.

FIG. 2A also shows example simplified user interfaces 260 and 270 according to alternative embodiments. Simplified user interface 260 includes a stimulation channel group controller 261 in the form of a rotator knob and a representative stimulus level display 262. Simplified user interface 270 includes a stimulation channel group controller 271 in the form of a set of up/down buttons and a representative stimulus level display 272. Simplified user interfaces 260 and 270 may have substantially the same functionality as simplified user interface 250 except with different mechanisms for adjusting a representative stimulus level.

The simplified user interfaces 250, 260, and 270 are shown in FIG. 2A as being displayed via a graphical user interface. However, in some embodiments, the simplified user interfaces may correspond to tangible mechanisms, such as, for example, physical sliders, physical rotator knobs, physical up/down buttons, or other similarly intuitive physical/tangible controller mechanisms. In some embodiments, the physical mechanisms may be located on the hearing prosthesis. In other embodiments, the physical mechanisms may be located on controller devices associated with the hearing prosthesis.

In operation, changes to the stimulation profile of the cochlear implant made via the complex user interface 200 may be reflected as changes in the simplified user interface 250, such as (i) changes to the representative stimulus level shown in the representative stimulus level display 254 and (ii) changes to the position of the slider 253 on the slider bar 252 of the stimulation channel group controller 251. Similarly, changes made to the stimulation profile of the cochlear implant by changing the position of the slider 253 on the slider bar 252 of the stimulation channel group controller 251 of the simplified user interface 250 may be reflected as changes to the individual C-levels and T-levels of individual stimulation channels shown in the complex user interface 200.

FIG. 2B shows an example of how adjustments to the stimulation channel group controller 251 of the simplified user interface 250 may result in changes to the stimulation profile of the cochlear implant as reflected in the complex user interface 200. The changes to the stimulation profile of the cochlear implant are shown in the complex user interface 200, where the complex user interface 200 reflects the individual C-level and T-level settings of each stimulation channel of the cochlear implant. In operation, changes to the stimulation profile of the cochlear implant may be made with either a simplified user interface or a complex user interface, and changes to the cochlear implant's stimulation profile that are made via either interface are reflected in the other interface.

Starting at step 1, the slider 253 on the slider bar 252 of the stimulation channel group controller 251 of the simplified user interface 250 is set to a first position that corresponds to a representative stimulus level of 117 as shown by the representative stimulus level display 254.

At step 2, the slider 253 has been moved up on the slider bar 252 of the stimulation channel group controller 251 to increase the representative stimulus level from 117 to 123 as shown by the representative stimulus level display 254. Changing the representative stimulus level via the simplified user interface 250 changes the cochlear implant's stimulation profile (i.e., the collection of settings for the stimulation channels of the cochlear implant). As shown in the complex user interface 200, the sliders corresponding to the individual C-levels and T-levels for the individual stimulation channels in the group of stimulation channels 208 have moved up relative to their previous settings—the previous C-levels and T-levels for each stimulation channel are shown by a shaded slider on each channel slider bar of the complex user interface 200. Similarly, the values for the C-levels 203 and T-levels 204 shown in box 202 along the bottom of the complex user interface 200 contain new numerical values for the C-levels 203 and T-levels 204 for each stimulation channel relative to their previous settings.

In the embodiment shown in FIG. 2B, the representative stimulus level is increased by 6 units from 117 to 123, and each C-level and T-level of the each stimulation channel of the cochlear implant is also increased by 6 units, as reflected in the complex user interface 200. However, in alternative embodiments, adjusting the representative stimulus level via the simplified user interface 250 may change only the C-levels or only the T-levels of the stimulation channels. In some embodiments, adjusting the representative stimulus level via the simplified user interface 250 by X units may change the C-levels and/or the T-levels of the stimulation channels by some number of units that is greater than or less than X units, i.e., a change in the representative stimulus level may not correspond to a one-to-one ratio change in the C-levels and/or T-levels. Additionally, the concept of interrelating simplified and complex user interfaces, and changing stimulation levels of a group of stimulation channels via changes to a representative stimulus level corresponding to the group of stimulation channels may be equally applicable to cochlear implant systems that may use stimulation channel levels that may be different than the C-levels and/or T-levels described herein.

FIG. 2C shows an example embodiment where adjustments made to a simplified user interface 250 with more than one channel group controller may result in changes to the stimulation profile of the cochlear implant as reflected in the complex user interface 200.

The simplified user interface 250 shown in FIG. 2C includes (i) a first stimulation channel group controller 251 corresponding to a first stimulation channel group 210 (which includes stimulation channels 12-22), and (ii) a second channel group controller 255 corresponding to a second stimulation channel group 211 (which includes stimulation channels 1-11).

The first stimulation channel group controller 251 may include a first slider bar 252 and a first slider 253, and the second stimulation channel group controller 255 may include a second slider bar 256 and a second slider 257. The first stimulation channel group controller 251 may be configured to adjust the stimulation levels (e.g., C-levels, T-levels, or other similar stimulation levels) of the first group of stimulation channels 210, and the second stimulation channel group controller 255 may be configured to adjust the stimulation levels of the second group of stimulation channels 211.

The first stimulation channel group controller 251 may also include a first representative stimulus level indicator 254 and a second representative stimulus level indicator 258. The first representative stimulus level indicator 254 may be configured to display a first representative stimulus level corresponding to the first channel group 210, and the second representative stimulus level indicator 258 may be configured to display a second representative stimulus level corresponding to the second channel group 211. In the embodiment shown in FIG. 2C, the first representative stimulus level indicator 254 shows a first representative stimulus level of 123 for the first channel group 210, and the second representative stimulus level indicator 258 shows a second representative stimulus level of 111 for the second channel group 211. In this particular embodiment, the first representative stimulus level corresponds to the mean of the C-levels for stimulation channels 12-22, and the second representative stimulus level corresponds to the average of the C-levels for stimulation channels 1-11. However, in other embodiments, the representative stimulus level for a particular channel group (e.g., the first group of stimulation channels 210 or the second group of stimulation channels 211) may correspond to a maximum stimulus level of the stimulation channels of the channel group, a minimum stimulus level of the stimulation channels of the channel group, or a median stimulus level of the stimulation channels of the channel group. In some embodiments, the representative stimulus level for a particular channel group may correspond to some other numerical value that may be based at least in part on a stimulation level of a stimulation channel in the particular group of two or more stimulation channels that may be controlled by a particular corresponding stimulation channel group controller.

In operation, adjustments to the first stimulation channel group controller 251 and the second stimulation channel group controller 255 of the simplified user interface 250 may result in changes to the stimulation profile of the cochlear implant as reflected in the complex user interface 200.

Starting at step 1, the first slider 253 on the first slider bar 252 of the first stimulation channel group controller 251 is set to a first position that corresponds to a first representative stimulus level of 123 as shown by the first representative stimulus level display 254. Also, the second slider 257 on the second slider bar 256 of the first stimulation channel group controller 255 is set to a second position that corresponds to a second representative stimulus level of 111 as shown by the second representative stimulus level display 258.

At step 2, the first slider 253 has been moved down on the first slider bar 252 of the first stimulation channel group controller 251 to reduce the first representative stimulus level from 123 to 116 as shown in the first representative stimulus level display 254. Also, the second slider 257 has been moved up on the second slider bar 256 of the second stimulation channel group controller 255 to increase the second representative stimulus level from 111 to 120 as shown in the second representative stimulus level display 258.

Changing the first and second representative stimulus levels via the simplified user interface 250 changes the cochlear implant's stimulation profile (i.e., the collection of settings for the stimulation channels of the cochlear implant). As shown in the complex user interface 200, the sliders corresponding to the individual C-levels and T-levels for the stimulation channels in the first group of stimulation channels 210 have moved down relative to their previous settings, and the sliders corresponding to the individual C-levels and T-levels for the stimulation channels in the second group of stimulation channels 211 have moved up relative to their previous settings—the previous C-levels and T-levels for each stimulation channel are shown by a shaded slider on each channel slider bar of the complex user interface 200. Similarly, the values for the C-levels 203 and T-levels 204 shown in box 202 along the bottom of the complex user interface 200 contain new numerical values for the C-levels 203 and T-levels 204 for each stimulation channel relative to their previous settings.

Additional simplified user interface embodiments may have three, four, or more stimulation channel group controllers along with optional representative stimulus level displays corresponding to each stimulation channel group controller. In these additional embodiments, individual stimulation channel group controllers may be configured to adjust representative stimulus levels of corresponding groups of two or more stimulation channels, where changes to a stimulation channel group's representative stimulus level made via the simplified user interface may be reflected as changes to the stimulation levels (e.g., C-levels, T-levels, or other similar stimulation levels) of the individual stimulation channels of the corresponding groups of two or more stimulation channels shown in a complex user interface, and vice versa.

As indicated herein, advanced training, skill, or experience is not required to use the simplified user interface 250 effectively. Thus, the simplified user interface 250 may be particularly advantageous in cities and towns that have a shortage of properly trained professionals with the ability and skill to use a sophisticated interface like the complex user interface 200 for fitting a hearing prosthesis to a recipient. The simplified user interface 250 may be particularly advantageous to some prosthesis recipients when they wish to adjust the fitting parameters of their prosthesis without the assistance of a professional and lack the skill and/or experience to adjust the fitting parameters with a sophisticated interface like the complex user interface 200.

5. Computing Devices for Displaying User Interfaces

Figure 3:
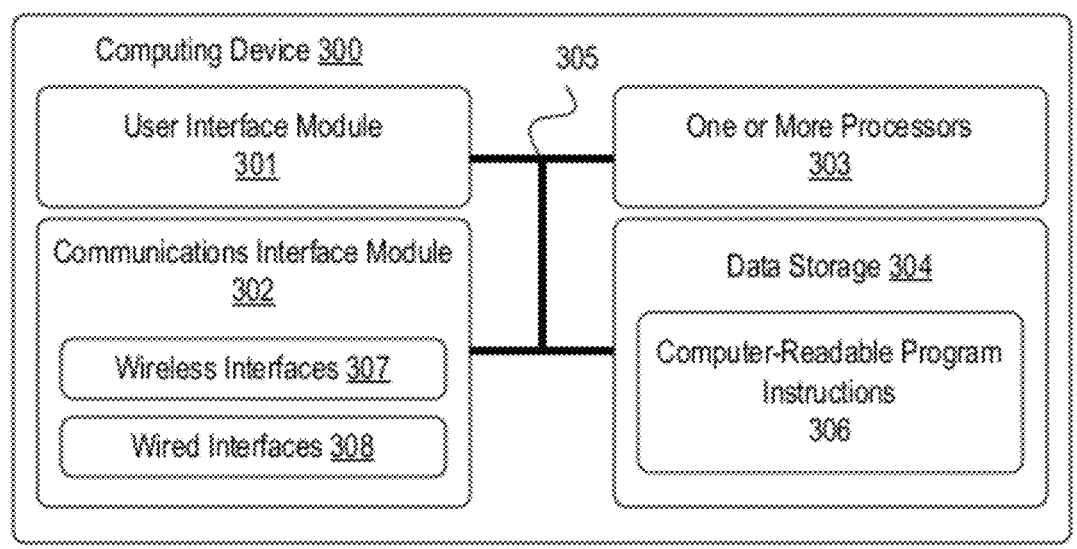
FIG. 3 shows an example of a computing device that may be configured to display various embodiments of the simplified and complex user interfaces.

FIG. 3 shows a block diagram of an example of a computing device 300 that may be configured to display the user interfaces described herein, such as, for example, the complex user interface 200 or the simplified user interfaces 250, 260, and/or 270 according to some embodiments of the disclosed systems and methods. The computing device 300 may include a user interface module 301, a communications interface module 302, one or more processors 303, and data storage 304, all of which may be linked together via a system bus or other connection mechanism 305.

The user interface module 301 may be configured to send data to and/or receive data from external user input/output devices. For example, the user interface module 301 may be configured to send/receive data to/from user input devices such as a keyboard, a keypad, a touch screen, a computer mouse, a track ball, a joystick, and/or other similar devices, now known or later developed. The user interface module 301 may also be configured to provide output to user display devices, such as one or more cathode ray tubes (CRT), liquid crystal displays (LCD), light emitting diodes (LEDs), displays using digital light processing (DLP) technology, printers, light bulbs, and/or other similar devices, now known or later developed. The user interface module 301 may also be configured to generate audible output(s), such as a speaker, speaker jack, audio output port, audio output device, earphones, and/or other similar devices, now known or later developed.

In some embodiments, the user interface module 301 may include or be communicatively coupled to an LCD or similar type of touch screen. The touch screen may be configured to display a user interface such as the interfaces described with respect to FIGS. 2A-C. The touch screen may also be configured to receive commands from a user, such as commands to adjust stimulation channel group controllers described with respect to FIGS. 2A-C.

The communications interface module 302 may include one or more wireless interfaces 207 and/or wired interfaces 208 that are configurable to communicate via a communications connection to the cochlear implant 100 (FIG. 1A), to another type of hearing prosthesis, or to other computing devices. The wireless interfaces 207 may include one or more wireless transceivers, such as a Bluetooth transceiver, a Wi-Fi transceiver, a WiMAX transceiver, and/or other similar type of wireless transceiver configurable to communicate via a wireless protocol. The wired interfaces 208 may include one or more wired transceivers, such as an Ethernet transceiver, a Universal Serial Bus (USB) transceiver, or similar transceiver configurable to communicate via a twisted pair wire, a coaxial cable, a fiber-optic link or a similar physical connection.

The one or more processors 303 may include one or more general purpose processors (e.g., microprocessors manufactured by Intel or Advanced Micro Devices) and/or one or more special purpose processors (e.g., digital signal processors, application specific integrated circuits, etc.). The one or more processors 303 may be configured to execute computer-readable program instructions 306 that are contained in the data storage 304 and/or other instructions based on algorithms described herein.

The data storage 304 may include one or more computer-readable storage media that can be read or accessed by at least one of the processors 303. The one or more computer-readable storage media may include volatile and/or non-volatile storage components, such as optical, magnetic, organic or other memory or disc storage, which can be integrated in whole or in part with at least one of the processors 303. In some embodiments, the data storage 304 may be implemented using a single physical device (e.g., one optical, magnetic, organic or other memory or disc storage unit), while in other embodiments, the data storage 304 may be implemented using two or more physical devices.

The data storage 304 may include computer-readable program instructions 306 and perhaps additional data. In some embodiments, the data storage 304 may additionally include storage required to perform at least part of the herein-described methods and algorithms and/or at least part of the functionality of the systems described herein.

6. Simplified User Interface Methods of Operation

Figure 4A:
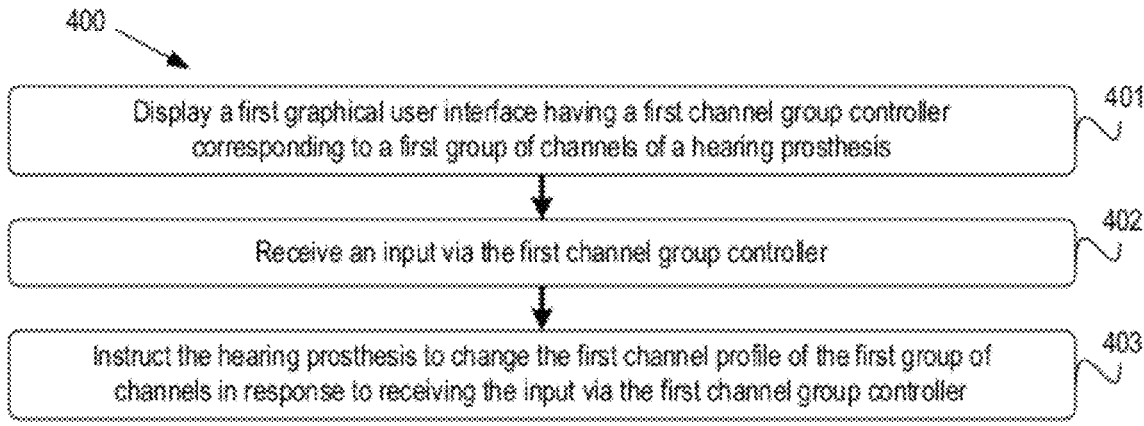
FIGS. 4A-4B show example methods that may be implemented by a simplified user interface configured to adjust the stimulation profile of a cochlear implant according to some embodiments of the disclosed systems and methods.
Figure 4B:
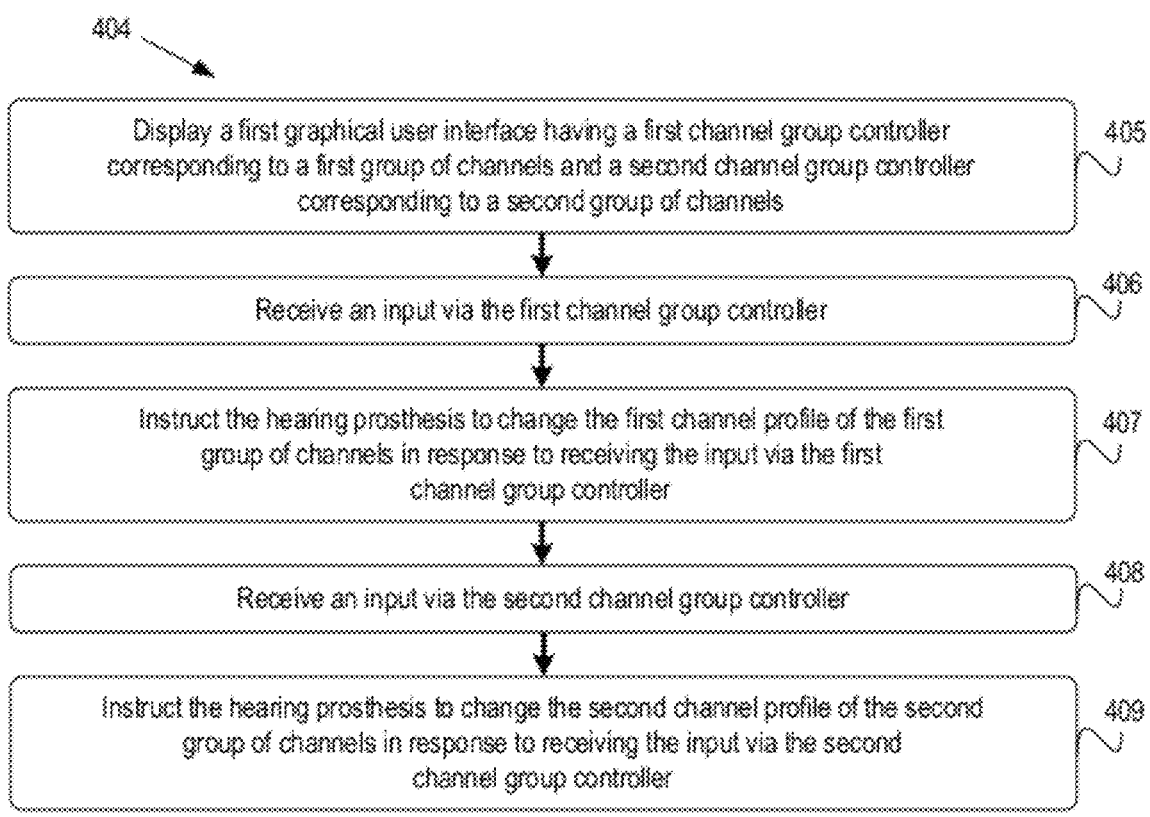

FIGS. 4A-4B show example methods that may be implemented in some embodiments by a user interface configured to adjust a channel profile of a hearing prosthesis such as, for example, an acoustic hearing aid, a bone anchored hearing aid, a direct acoustic cochlear stimulation device, an auditory brain stem implant, and/or a cochlear implant.

FIG. 4A shows an example method 400 that may be used with a hearing prosthesis according to some embodiments. The method 400 may be implemented by a simplified user interface with a single channel group controller. Method 400 begins at block 401, where a first user interface having a first channel group controller corresponding to a first group of channels of a hearing prosthesis is displayed. In some embodiments, the first user interface of block 401 may be similar to the simplified user interface 250 with stimulation channel group controller 251 as shown in FIGS. 2A-B. In some embodiments, the first user interface of block 401 may alternatively be similar to the simplified user interface 260 with stimulation channel group controller 261 or simplified user interface 270 with stimulation channel group controller 271.

In some embodiments, the first user interface may be displayed by a computing device such as computing device 300 shown in FIG. 3. In some embodiments, the hearing prosthesis of block 401 may be similar to cochlear implant 100 shown in FIG. 1A, and the first group of channels of block 401 may include stimulation channels configured to generate stimulation signals similar to stimulation signal 191 shown in FIG. 1C. In other embodiments, the hearing prosthesis of block 401 may be an acoustic hearing aid, a bone anchored hearing aid, a direct acoustic cochlear stimulation device, an auditory brain stem implant, or any other hearing prosthesis that may be configured to generate acoustic signals, mechanical vibration signals, or electrical signals at configurable frequencies and intensities.

In some embodiments for use with cochlear implants, the first user interface may be configured to display a unit value corresponding to a first representative stimulus level for the first stimulation profile. The first representative stimulus level may be displayed by a representative stimulus level indicator such as representative stimulus level indicator 254 shown in FIG. 2B. The first representative stimulus level may be similar to the representative stimulus levels shown and described herein with respect to FIGS. 2A-C.

At block 402, an input may be received via the first channel group controller. In some embodiments, the input may be received via a computing device touch screen configured to display the first channel group controller, as described with respect to FIG. 3. In other embodiments, the input may be received via any of the other input devices of the computing device described with respect FIG. 3.

At block 403, the hearing prosthesis may be instructed to change the first channel profile of the first group of channels of the hearing prosthesis in response to receiving the input via the first channel group controller. For embodiments where the hearing prosthesis is a cochlear implant, the cochlear implant at block 403 may be instructed to change the first stimulation profile of the first of stimulation channels in response to receiving the input via the first stimulation channel group controller. For example, changing the first stimulation profile of the first group of stimulation channels of the cochlear implant may be similar to the procedures shown and described herein with respect to FIG. 2B.

FIG. 4B shows an example method 404 that may be implemented by a simplified user interface with a two channel group controllers. Example method 404 begins at block 405, where a first user interface is displayed. The first user interface of block 405 may have (i) a first channel group controller corresponding to a first group of channels and (ii) a second channel group controller corresponding to a second group of channels. In some embodiments, the first user interface of block 405 may be similar to the simplified user interface 250 with first stimulation channel group controller 251 and second stimulation channel group controller 258, as shown in FIG. 2C. In some embodiments, the first user interface of block 405 may alternatively be similar to either (i) the simplified user interface 260 with two stimulation channel group controllers similar to controller 261 or (ii) the simplified user interface 270 with two stimulation channel group controllers similar to controller 271.

In some embodiments, the first user interface may be configured to display (i) a first unit value corresponding to a first representative intensity level for the first channel profile and (ii) a second unit value corresponding to a second representative intensity level for the second channel profile. In some embodiments, the first representative intensity level may be displayed by a representative intensity level indicator such as representative stimulus level indicator 254, and the second representative intensity level may be displayed by a representative intensity level indicator such as the second representative stimulus level indicator 258, as shown and described herein with respect to FIG. 2C. The first and second representative intensity levels may correspond to values that are based at least in part on an intensity level of a channel in the first and second groups of channels, respectively, such as, for example, the first and second stimulation channel groups as shown and described herein with respect to FIG. 2C.

At block 406, an input may be received via the first channel group controller. In some embodiments, the input may be received via a computing device touch screen configured to display the first channel group controller, such as the touch screen described with respect to FIG. 3. In other embodiments, the input may be received via any of the other input devices of the computing device described with respect FIG. 3.

At block 407, the hearing prosthesis may be instructed to change the first channel profile of the first group of channels in response to receiving the input via the first channel group controller. For example, changing the first channel profile of the first group of channels may be similar to the procedure described herein with respect to FIG. 2C, where a change to the first representative stimulus level via the first stimulation channel group controller 254 may result in a change to the first stimulation profile of the first group of stimulation channel 210.

At block 408, an input may be received via the second channel group controller. In some embodiments, the input may be received via a computing device touch screen configured to display the second channel group controller, such as the touch screen described with respect to FIG. 3. In other embodiments, the input may be received via any of the other input devices of the computing device described with respect FIG. 3.

At block 409, the hearing prosthesis may be instructed to change the second channel profile of the second group of channels in response to receiving the input via the second channel group controller. For example, changing the second channel profile of the second group of channels may be similar to the procedures shown and described herein with respect to FIG. 2C, where a change to the second representative stimulus level via the second stimulation channel group controller 258 may result in a change to the stimulation profile of the second group of stimulation channel 211.

Although FIG. 4B shows blocks 406 through 409 in sequential order, it is understood that the functions of blocks 408 and 409 could be performed prior to the functions of blocks 406 and 407, or vice versa, without departing from the envisioned functionality of the method 404.

7. Algorithms for Implementing Simplified User Interface Methods of Operation

Figure 5:
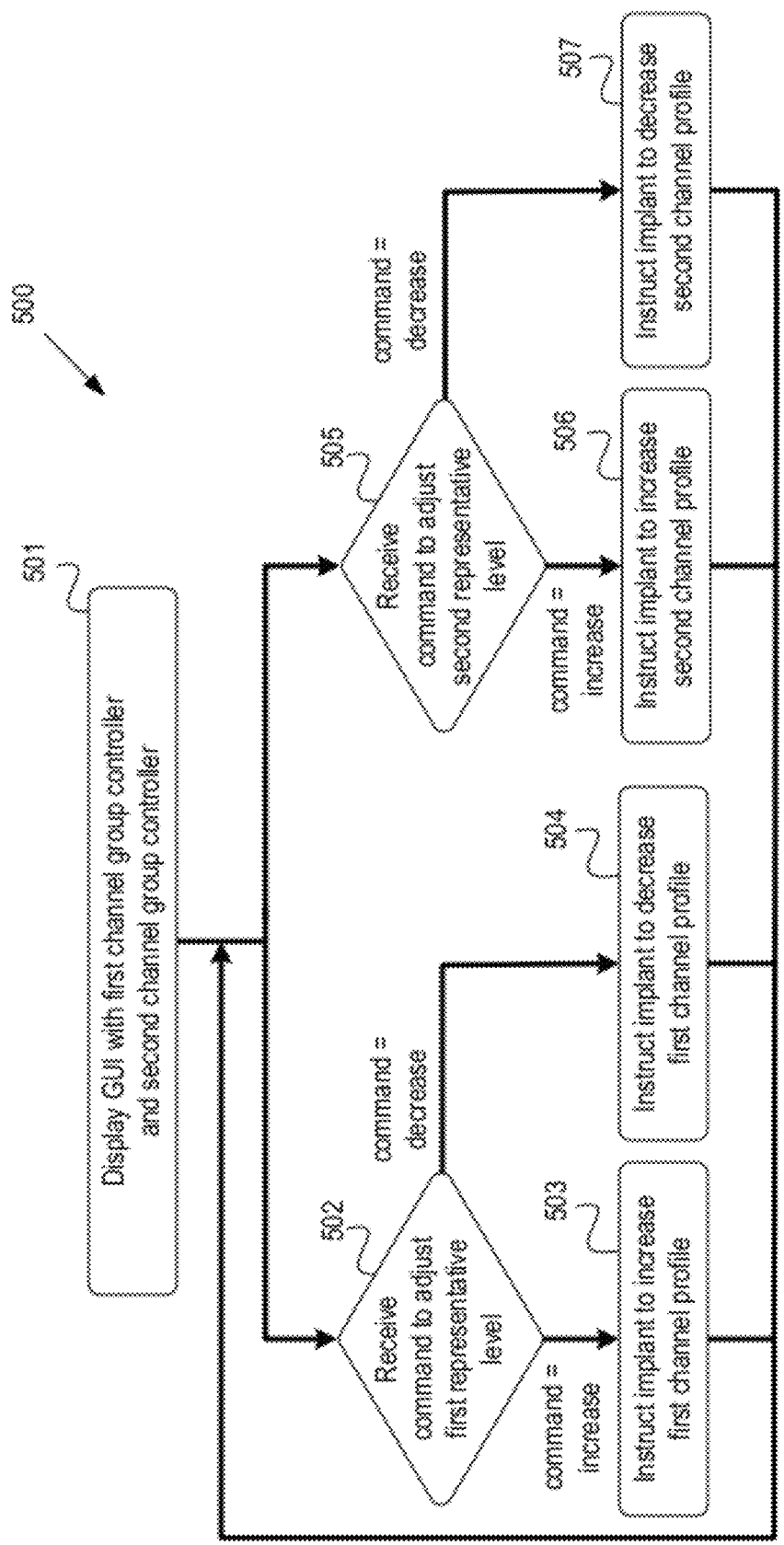
FIG. 5 shows an example algorithm that may be implemented by a simplified user interface configured to adjust the stimulation profile of a cochlear implant according to some embodiments of the disclosed systems and methods.

FIG. 5 shows an example algorithm 500 that may be implemented by a simplified user interface configured to adjust settings of a hearing prosthesis according to some embodiments of the disclosed systems and methods. In some embodiments, the simplified user interface may be similar to the simplified user interface 250 shown in FIG. 2C. The algorithm 500 may be stored in data storage and encoded in the form of computer-readable program instructions for execution by a computing device, such as computing device 300 (FIG. 3).

At step 501, a computing device may display a user interface with a first channel group controller and a second channel group controller, such as, for example, the first and second stimulation channel group controllers shown and described herein with respect to FIG. 2C and FIG. 4.

At step 502, the computing device may receive a command to adjust the first representative intensity level. If the command is a command to increase the first representative intensity level of the first channel group, then the computing device may instruct the hearing prosthesis to change the first channel profile accordingly at step 503. In some embodiments, instructing the hearing prosthesis to change the channel profile may include sending instructions to an processor unit associated with the hearing prosthesis, such as, for example, the external assembly 142 (FIG. 1A) of the cochlear implant. In embodiment for use with cochlear implants, the instructions may be sent to the external assembly so that the external assembly can adjust the stimulation channel settings of the implant. If the command is a command to decrease the first representative intensity level of the first channel group, then the computing device may instruct the hearing prosthesis to adjust the first channel profile accordingly at step 504.

At step 505, the computing device may receive a command to adjust the second representative intensity level. If the command is a command to increase the second representative intensity level of the second channel group, then the computing device may instruct the hearing prosthesis (or the external assembly 142 in the case of a cochlear implant) to change the second channel profile accordingly at step 506. If the command is a command to decrease the second representative intensity level of the second channel group, then the computing device may instruct the hearing prosthesis to adjust the second channel profile accordingly at step 507.

The algorithm 500 may be performed during the process of initially fitting the hearing prosthesis to the recipient shortly after the recipient has received the hearing prosthesis. Alternatively, or additionally, algorithm 500 may also be performed one or more times after the initial fitting as needed or desired.

8. Methods for Cochlear Implant Fitting Using a Simplified User Interface

Simplified user interfaces like the ones described herein may be used to fit a cochlear implant (or other hearing prosthesis) to an implant recipient. Because a simplified user interface may have many fewer controls and options when compared to a complex user interface similar to the complex interfaces described herein, a simplified user interface may be implemented on a comparatively wider range of platforms more easily than a complex user interface. For example, a simplified user interface may be implemented on a hand-held computing device, such as a hand-held fitting system or as an application on a smart phone or other type of small and/or portable computing device. Fitting a cochlear implant with a simplified user interface according the methods described herein may be performed by an audiologist or similarly trained professional, or the fitting may additionally or alternatively in some cases be performed by the actual implant recipient.

However, because a simplified user interface may have fewer controls and options compared to a complex user interface, it may be desirable to have fitting system software that may be configured to automatically determine one or more initial configuration settings for the cochlear implant. Such fitting system software may be implemented within a cochlear implant, such as cochlear implant 100 (FIG. 1A), or on a computing device separate from the cochlear implant, such as computing device 300 (FIG. 3).

Figure 6:
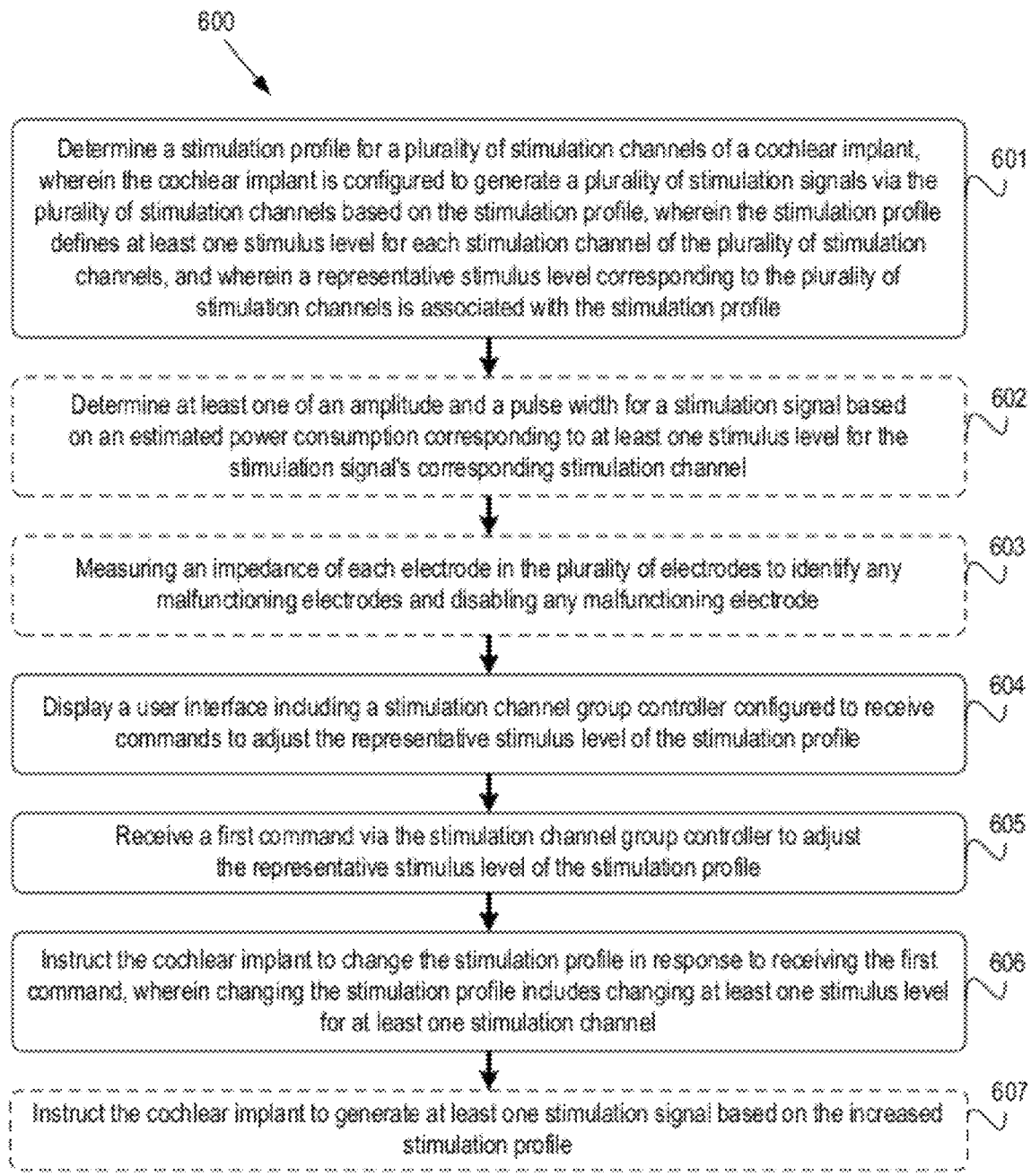
FIG. 6 shows an example method for using a simplified user interface to fit a cochlear implant to an implant recipient according to some embodiments of the disclosed systems and methods.

FIG. 6 shows one example embodiment of a method 600 for fitting a cochlear implant to an implant recipient using a simplified user interface according to some embodiments of the disclosed systems and methods.

The method 600 begins at block 601, where a stimulation profile for a plurality of channels of a cochlear implant is determined. In some embodiments, the cochlear implant may be configured to generate a plurality of stimulation signals (e.g., stimulation signal 191 shown in FIG. 1C.) via a plurality of stimulation channels based on the stimulation profile. The stimulation profile may define at least one stimulus level (e.g., a C-level, T-level, or other stimulus level) for each stimulation channel of the plurality of stimulation channels.

In some embodiments, the plurality of stimulation channels may correspond to all the stimulation channels of the cochlear implant, as shown, for example, in FIGS. 2A-B. In other embodiments, the plurality of stimulation channels may correspond to less than all of the stimulation channels of the cochlear implant, as shown, for example, in FIG. 2C, where the plurality of stimulation channels may include a first stimulation channel group 210 and/or a second stimulation channel group 211 (FIG. 2C).

The stimulation profile may also have a corresponding representative stimulus level. The representative stimulus level may be similar to the representative stimulus levels shown and described herein with respect to FIGS. 2A-C. In some embodiments, the representative stimulus level for the simulation profile may be displayed by a representative stimulus level indicator, such as indicators 254, 258, 262, or 272 (FIGS. 2A-C). In some embodiments, the representative stimulus level may be displayed in both the simplified user interface 250 and the complex user interface 200 (FIGS. 2A-2C).

In some embodiments, the stimulation profile for the cochlear implant may be based on an estimated equal loudness contour determined for the plurality of stimulation channels. The estimated equal loudness contour may be based on the C-level setting for each stimulation channel configured to cause sounds at the respective C-levels of each stimulation to be perceived by the implant recipient as substantially the same sound level, i.e., substantially equally loud. In some embodiments, the estimated equal loudness contour may be based on one or more Neural Response Telemetry (NRT) measurements. In operation, Neural Response Telemetry may be used to measure neural activity within the implant recipient's cochlea in response to one or more simulation signals generated by the implant. In some embodiments, the stimulation profile may be based on measured neural responses to stimulation signals.

In some embodiments, electrically evoked compound action potential (ECAP) thresholds across the plurality of stimulation channels (i.e. the minimum stimulus levels which evoke a detectable neural response at each stimulation channel) can be used as an estimate of the shape of the equal loudness contour. Co-pending application Ser. No. 10/569,054 describes systems and methods for the automatic measurement of ECAP thresholds, and co-pending application Ser. No. 12/809,579 describes systems and methods for estimating equal loudness contours based on ECAP thresholds. The entire contents of the Ser. Nos. 10/569,054 and 12/809,579 applications are incorporated herein by reference.

In addition to determining a stimulation profile for the cochlear implant, the method 600 may also optionally include (i) determining at least one of an amplitude and/or pulse width for a pulse of a stimulation signal 602, and/or (ii) measuring an impedance of one or more electrodes to identify and/or disable any malfunctioning electrode 603. The functions of optional blocks 602 and 603 may be performed before or after the functions of block 601—the order of the functions of blocks 601, 602, and 603 is not critical to the envisioned functionality of the disclosed systems and methods.

In block 602, the amplitude and/or pulse width of a current pulse of one or more stimulation signals may be determined. The determination of the amplitude and/or pulse width of a current pulse may be based on an estimated power consumption corresponding to a stimulus level for the stimulation signal's corresponding stimulation channel. In some embodiments, the amplitude and/or pulse width for one or more stimulation channels may be selected to maximize the power efficiency of the cochlear implant. In some embodiments, the power efficiency of the cochlear implant may be based in part on the configuration of the cochlear implant's sound processing unit.

In block 603, the impedance of one or more (or all) of the electrodes of the electrode array of the cochlear implant may be measured to identify and/or disable any malfunctioning electrodes.

At block 604, a simplified user interface, such as simplified user interfaces 250, 260, or 270 as shown in FIGS. 2A-C may be displayed. The simplified user interface may include one or more stimulation channel group controllers, such as the stimulation channel group controllers shown and described herein with respect FIGS. 2A-C. The stimulation channel group controllers may be configured to receive commands to adjust the representative stimulus level of the stimulation profile (or profiles) determined in block 601. In some embodiments, the simplified user interface may also include a representative stimulus level indicator, such as indicators 254, 258, 262, or 272 (FIGS. 2A-C) or other similar indicators.

A first command to adjust the representative stimulus level corresponding to the stimulation profile may be received at block 605. And at block 606, the cochlear implant may be instructed to change its stimulation profile in response to receiving the first command. Changing the stimulation profile of the cochlear implant may include changing at least one stimulation level for at least one stimulation channel of the cochlear implant. In some embodiments, changing the stimulation profile of the cochlear implant may be similar to the methods of changing a cochlear implant's stimulation profile as shown and described herein with respect to FIGS. 2A-C. At optional block 607, the cochlear implant 100 may be instructed to generate at least one stimulation signal based on the changed stimulation profile.

In some embodiments, the stimulation profile determined at block 601 may correspond to C-level or T-level settings for the cochlear implant that are inaudible, barely audible, or perhaps comfortably audible to the cochlear implant recipient. Initially setting the stimulation profile at block 401 to low stimulation levels may serve as a safety precaution to the implant recipient to avoid an initial stimulation profile that is uncomfortably loud, or perhaps even dangerously loud.

In some embodiments, the first command of block 605 may be a command to increase the representative stimulus level of the stimulation profile of the cochlear implant by a single unit value. For example, if the representative stimulus level is currently 92, then the first command might be a command to increment the representative stimulus level to 93. As described with respect to FIGS. 2A-C, the change in the representative stimulus level shown in the simplified user interface may cause a change in the stimulation profile of the cochlear implant. In these embodiments, limiting the increase of the representative stimulus level to a single unit value at a time may operate as a safety function to prevent the stimulation profile from being increased too rapidly so that the stimulation profile does not become uncomfortably loud (or even dangerously loud) unexpectedly.

As an additional safety precaution, and optionally in concert with the single-step increase functionality described above, the cochlear implant may be further instructed in some embodiments to generate at least one stimulation signal based on the increased stimulation profile at block 607. By instructing the cochlear implant to generate at least one stimulation signal based on the increased stimulation profile, the implant recipient can listen to sound at the increased stimulation profile before choosing to further increment the representative stimulus level.

In some embodiments, a simplified user interface may prompt the implant recipient (or other user) to accept the increased stimulation profile. In such embodiments, if the user interface does not receive an indication that the recipient (or other user) has accepted the increased stimulation profile, the cochlear implant may be instructed to return to the previous stimulation profile.

In other embodiments, the simplified user interface may not prompt the implant recipient (or other user) to accept the increased stimulation profile. In embodiments where the simplified user interface does not prompt the implant recipient (or other user) to accept the increased stimulation profile, the user's acceptance of the increased stimulation profile may be inferred from either (i) the absence of further inputs via the stimulation channel group controller to adjust the representative stimulus level or (ii) receiving an input via the stimulation channel group controller to increase the representative stimulus level by an additional single unit value. Similarly, receiving an input via the stimulation channel group controller to decrement the representative stimulus level in response to the stimulation signal at the increased stimulation profile may indicate that the increased stimulation profile is uncomfortably loud.

In some embodiments, the above-described safety features may be activated when either (or both) of the user interface and the cochlear implant are operating in a safety mode. In such embodiments, the representative stimulus level may be moved up or down by more than a single unit value as long as the system (including the user interface and/or the implant) has not been placed into the safety mode. In other embodiments, the above-described safety features may activated as part of a default configuration. In still other embodiments, the above-described safety features may be part of the system's normal operating mode such that operation in a separate safety mode may not be required.

9. Algorithms for Implementing Fitting Methods with Simplified User Interfaces

Figure 7:
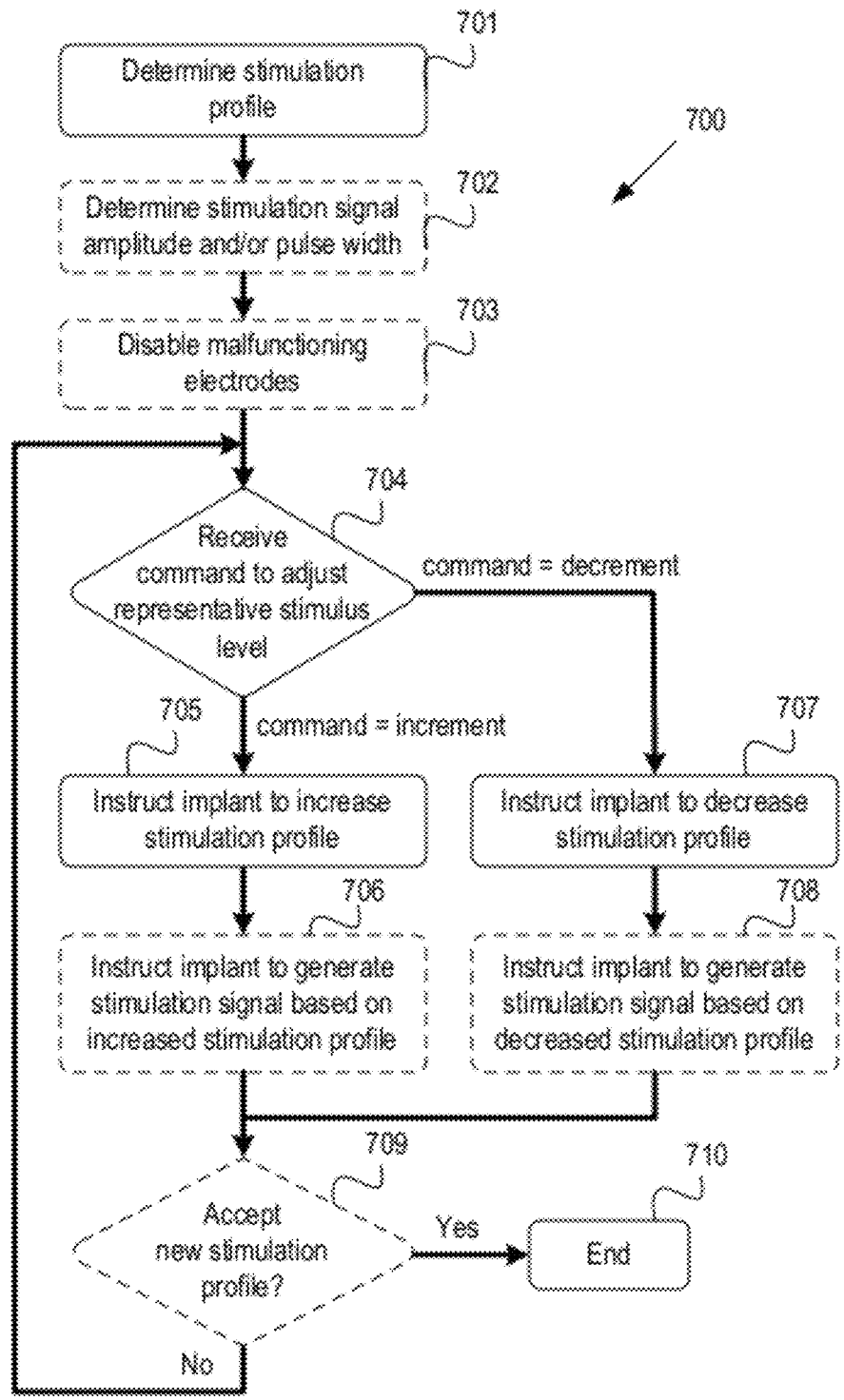
FIG. 7 shows an example algorithm that may be implemented by a simplified user interface to fit a cochlear implant to an implant recipient according to some embodiments of the disclosed systems and methods.

FIG. 7 shows an example algorithm 700 for fitting a cochlear implant with a simplified user interface, such as simplified user interface 250 (FIGS. 2A-C), according to some embodiments of the disclosed systems and methods. The algorithm 700 may be stored in data storage and encoded in the form of computer-readable program instructions for execution by a computing device, such as computing device 300 (FIG. 3).

At step 701, a stimulation profile for a cochlear implant is determined as described herein with respect to FIG. 6. At optional step 702, a stimulation signal amplitude and/or pulse width may be determined, and at optional step 703, any malfunctioning electrodes may be disabled. The simulation signal amplitude and/or pulse width may be determined based on an estimated power consumption corresponding to one or more stimulus levels as described herein with respect to FIG. 6. The disabling of malfunctioning electrodes may be performed as described also herein with respect to FIG. 6. Additionally the order of algorithm steps 701, 702, and 703 is not critical to the functionality of the algorithm 700.

At step 704, the computing device may receive a command to adjust the representative stimulus level of the stimulation profile of the cochlear implant. If the command is a command to increment the representative stimulus level, then the computing device may instruct the cochlear implant to increase the stimulation profile accordingly at step 705. In some embodiments, instructing the cochlear implant to change the stimulation profile may include sending instructions to the external assembly 142 (FIG. 1A) of the cochlear implant so that the external assembly can adjust the stimulation channel settings of the implant. In some embodiments, increasing the stimulation profile of the cochlear implant may be accomplished according to the methods shown and described herein with respect to FIGS. 2A-C. After instructing the cochlear implant to increase the stimulation profile at step 705, the computing device may optionally instruct the cochlear implant to generate at least one stimulation signal based on the increased stimulation profile at step 706.

If the command is a command to decrement the representative stimulus level, then the computing device may instruct the cochlear implant (or the external assembly 142 of the cochlear implant) to decrease the stimulation profile accordingly at step 707. In some embodiments, decreasing the stimulation profile of the cochlear implant may be accomplished according to the methods shown and described herein with respect to FIGS. 2A-C. After instructing the cochlear implant to decrease the stimulation profile at step 707, the computing device may optionally instruct the cochlear implant to generate a stimulation signal based on the decreased stimulation profile at step 708.

In some embodiments, the simplified user interface may optionally prompt a user to accept the new stimulation profile at step 709. If the user accepts the new stimulation profile step 709, then the algorithm 700 may end at step 710. But if the user does not accept the new stimulation profile at step 709, then the algorithm may return to step 704 to receive another command to adjust the representative stimulus level.

In embodiments that do not include optional step 709, the computing device may simply return to step 704 and wait to receive a command to adjust the representative stimulus level after performing step 705 or 707 (or optionally steps 706 or 708, depending on the embodiment).

The algorithm 700 may be performed during the process of initially fitting the cochlear implant to the recipient shortly after the cochlear implant has been implanted in the recipient's cochlea. Alternatively, or additionally, algorithm 700 may also be performed one or more times after the initial fitting as needed or desired.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method performed by a hearing prosthesis fitting system, the method comprising:
    displaying on a display screen of a computing device, a first graphical user interface comprising (i) a first channel group controller configured to control a channel profile of a first group of two or more channels of a hearing prosthesis, wherein the channel profile of the first group of channels comprises at least one intensity level for each channel in the first group of channels and (ii) a representative intensity level for the channel profile of the first group of channels, wherein the representative intensity level for the channel profile of the first group of channels comprises a numerical value based at least in part on one or more of (a) a mean of two or more intensity levels of the channels in the first group of channels, (b) a median of two or more intensity levels of the channels in the first group of channels, (c) a maximum of two or more intensity levels of the channels in the first group of channels, or (d) a minimum of two or more intensity levels of the channels in the first group of channels;
    receiving a command via the first graphical user interface to change the representative intensity level of the channel profile of the first group of channels of the hearing prosthesis; and
    in response to receiving the command to change the representative intensity level of the channel profile of the first group of channels of the hearing prosthesis, changing one or more intensity levels of one or more channels in the first group of channels of the hearing prosthesis.

2. The method of claim 1, further comprising:
    after changing one or more intensity levels of one or more channels in the first group of channels of the hearing prosthesis, instructing the hearing prosthesis to apply at least one stimulation signal at the changed one or more intensity levels to a recipient of the hearing prosthesis.

3. The method of claim 1, further comprising:
    determining at least one initial intensity level for each channel in the first group of channels based at least in part on an estimated equal loudness contour for the first group of channels, wherein the estimated equal loudness contour is based on an analysis of a measured neural response of a recipient of the hearing prosthesis to at least one stimulus applied to the recipient by the hearing prosthesis.

4. The method of claim 1, wherein for an individual channel in the first group of channels, the at least one intensity level is one or more of a threshold level and/or a maximum comfort level.

5. The method of claim 1, further comprising:
    determining whether a channel in the first group of channels is malfunctioning, and
    in response to determining that the channel is malfunctioning, disabling the malfunctioning channel.

6. The method of claim 1, wherein the first graphical user interface further comprises (i) a second channel group controller configured to control a channel profile of a second group of two or more channels of the hearing prosthesis, wherein the channel profile of the second group of channels comprises at least one intensity level for each channel in the second group of channels and (ii) a representative intensity level for the channel profile of the second group of channels, wherein the representative intensity level for the channel profile of the second group of channels comprises a numerical value based at least in part on one or more of (a) a mean of two or more intensity levels of the channels in the second group of channels, (b) a median of two or more intensity levels of the channels in the second group of channels, (c) a maximum of two or more intensity levels of the channels in the second group of channels, or (d) a minimum of two or more intensity levels of the channels in the second group of channels, and wherein the method further comprises:
    receiving a command via the first graphical user interface to change the representative intensity level of the channel profile of the second group of channels of the hearing prosthesis; and
    in response to receiving the command to change the representative intensity level of the channel profile of the second group of channels of the hearing prosthesis, changing one or more intensity levels of one or more channels in the second group of channels of the hearing prosthesis.

7. The method of claim 1, wherein changes made to the one or more intensity levels of the one or more channels in the first group of channels of the hearing prosthesis are viewable and modifiable via a second user interface comprising a plurality of channel controllers, wherein each channel controller of the second user interface is configured to individually control at least one intensity level for a single channel of the hearing prosthesis, and wherein a display associated with the second user interface displays information indicative of the at least one intensity level for each channel of the hearing prosthesis.

8. The method of claim 1, wherein the hearing prosthesis is one of a cochlear implant, an acoustic hearing aid, a bone anchored hearing aid, a direct acoustic stimulation device, or an auditory brain stem implant.

9. The method of claim 2, further comprising:
    after the hearing prosthesis has applied the at least one stimulation signal at the changed one or more intensity levels to the recipient, receiving via the first user graphical interface, a command to either (i) accept the changed one or more intensity levels or (ii) not to accept the changed one or more intensity levels;

in response to receiving a command to accept the changed one or more intensity levels, updating the channel profile of the first group of channels to reflect the changed one or more intensity levels; and in response to receiving a command not to accept the changed one or more intensity levels, configuring the channels in the first group of channels to the intensity levels they were at before the step of changing the one or more intensity levels of the first group of channels.

10. A fitting system for a hearing prosthesis, the fitting system comprising:

one or more processors; and tangible, non-transitory computer-readable memory comprising computer-executable instructions, wherein the instructions, when executed by the one or more processors, causes the fitting system to:

display on a display screen, a first graphical user interface comprising (i) a first channel group controller configured to control a channel profile of a first channel group of a hearing prosthesis, wherein the first channel profile of the first channel group comprises at least one intensity level for each channel in the first channel group, and (ii) a representative intensity level for the first channel profile of the first channel group, wherein the representative intensity level for the channel profile of the first channel group comprises a numerical value based at least in part on one or more of (a) a mean of two or more intensity levels of the channels in the first channel group, (b) a median of two or more intensity levels of the channels in the first channel group, (c) a maximum of two or more intensity levels of the channels in the first channel group, or (d) a minimum of two or more intensity levels of the channels in the first channel group;

receive a command via the first graphical user interface to change the representative intensity level of the channel profile of the first channel group of the hearing prosthesis; and in response to receiving the command to change the representative intensity level of the channel profile of the first channel group of the hearing prosthesis, change one or more intensity levels of one or more channels in the first channel group of the hearing prosthesis.

11. The fitting system of claim 10, wherein the system is further configured to:

after changing one or more intensity levels of one or more channels in the first channel group of the hearing prosthesis, instruct the hearing prosthesis to apply at least one signal to a recipient of the hearing prosthesis at the one or more changed intensity levels.

12. The fitting system of claim 10, wherein the system is further configured to:

determine at least one intensity level for each channel in the first channel group based at least in part on an estimated equal loudness contour for the first channel group, wherein the estimated equal loudness contour is based on an analysis of a measured neural response to at least one signal generated by the hearing prosthesis.

13. The fitting system of claim 10, wherein for an individual channel in the first channel group, the at least one intensity level is one or more of a threshold level and/or a maximum comfort level.

14. The fitting system of claim 10, wherein the system is further configured to:

determine whether a channel in the first channel group is malfunctioning; and in response to determining that the channel is malfunctioning, disable the malfunctioning channel.

15. The fitting system of claim 10, wherein the first graphical user interface further comprises (i) a second channel group controller configured to control a channel profile of a second channel group of the hearing prosthesis, wherein the channel profile of the second channel group comprises at least one intensity level for each channel in the second channel group, and (ii) a representative intensity level for the channel profile of the second channel group, wherein the representative intensity level for the channel profile of the second channel group comprises a numerical value based at least in part on one or more of (a) a mean of two or more intensity levels of the channels in the second channel group, (b) a median of two or more intensity levels of the channels in the second channel group, (c) a maximum of two or more intensity levels of the channels in the second channel group, or (d) a minimum of two or more intensity levels of the channels in the second channel group;

wherein the system is further configured to receive a command via the first graphical user interface to change the representative intensity level of the channel profile of the second channel group of the hearing prosthesis; and in response to receiving the command to change the representative intensity level of the channel profile of the second channel group of the hearing prosthesis, changing one or more intensity levels of one or more channels in the second channel group of the hearing prosthesis.

16. The fitting system of claim 10, wherein changes made via the first graphical user interface to the one or more intensity levels of the one or more channels of the first channel group are viewable and modifiable via a second user interface comprising a plurality of channel controllers, wherein individual channel controllers of the second user interface are configured to individually control intensity levels for individual channels of the hearing prosthesis, and wherein a display associated with the second user interface displays information indicative of the at least one intensity level for each channel of the hearing prosthesis.

17. The fitting system of claim 10, wherein the first channel group controller is one of a rotator icon, a slider icon, or an up/down button icon displayed within the first graphical user interface.

18. The fitting system of claim 10, wherein the hearing prosthesis is one of a cochlear implant, an acoustic hearing aid, a bone anchored hearing aid, a direct acoustic stimulation device, or an auditory brain stem implant.

19. The fitting system of claim 11, wherein the system is further configured to:

after the hearing prosthesis has applied the at least one signal at the changed one or more intensity levels to the recipient, receive via the first graphical user interface, a command to either (i) accept the changed one or more intensity levels or (ii) not to accept the changed one or more intensity levels;

in response to receiving a command to accept the changed one or more intensity levels, update the channel profile of the first channel group to reflect the changed one or more intensity levels; and in response to receiving a command not to accept the changed one or more intensity levels, configure the channels of the first channel group to the intensity levels they were at before the step of changing the one or more intensity levels of the first channel group.

20. A tangible, non-transitory computer-readable media with instructions stored thereon, wherein the instructions, when executed by one or more processors, cause a computing device communicatively coupled to a hearing prosthesis to:

display, on a display screen, a graphical user interface comprising a representative intensity level for a first channel group of the hearing prosthesis, wherein the first channel group comprises two or more channels of the hearing prosthesis, wherein each channel in the first channel group has at least one intensity level setting, and wherein the representative intensity level for the first channel group comprises a numerical value based at least in part on one or more of (a) a mean of two or more intensity level settings of the channels in the first channel group, (b) a median of two or more intensity level settings of the channels in the first channel group, (c) a maximum of two or more intensity level settings of the channels in the first channel group, and (d) a minimum of two or more intensity level settings of the channels in the first channel group;

receive a command via a first channel group controller to change the representative intensity level of the first channel group; and in response to receiving the command via the first channel group controller to change the representative intensity level of the first channel group, change one or more individual intensity levels of one or more individual channels in the first channel group of the hearing prosthesis.

21. The computer-readable media of claim 20, wherein the computing device is further configured to:

after changing one or more individual intensity levels for one or more individual channels in the first channel group of the hearing prosthesis, instruct the hearing prosthesis to apply at least one signal at the one or more changed intensity levels to a recipient of the hearing prosthesis.

22. The computer-readable media of claim 20, wherein the computing device is further configured to:

determine an initial intensity level setting for each channel in the first channel group based on an estimated equal loudness contour for one or more channels in the first channel group, wherein the estimated equal loudness contour is based on an analysis of a measured neural response of a recipient of the hearing prosthesis to at least one signal applied to the recipient by the hearing prosthesis.

23. The computer-readable media of claim 20, wherein for an individual channel, the at least one intensity level setting is one or more of a threshold level and/or a maximum comfort level.

24. The computer-readable media of claim 20, wherein the computing device is further configured to:

determining whether a channel in the first channel group is malfunctioning; and in response to determining that the channel in the first channel group is malfunctioning, disable the malfunctioning channel.

25. The computer-readable media of claim 20, wherein the graphical user interface further comprises (i) a representative intensity level for a second channel group, wherein the second channel group comprises two or more channels of the hearing prosthesis, wherein each channel in the second channel group has at least one intensity level setting, and wherein the representative intensity level for the second channel group comprises a numerical value based at least in part on one or more of (a) a mean of two or more intensity level settings of two or more channels in the second channel group, (b) a median of two or more intensity level settings of two or more channels in the second channel group, (c) a maximum of two or more intensity level settings of two or more channels in the second channel group, and (d) a minimum of two or more intensity level settings of two or more channels in the second channel group, wherein the computing device is further configured to:

receive a command via a second channel group controller to change the representative intensity level of the second channel group; and in response to receiving the command via the second channel group controller to change the representative intensity level of the second channel group, change one or more individual intensity levels for one or more individual channels in the second channel group of the hearing prosthesis.

26. The computer-readable media of claim 20, wherein the first channel group controller is one of (i) a rotator icon, a slider icon, or an up/down button icon displayed within the graphical user interface or (ii) a physical channel group controller comprising one of a rotator knob, a slider, or an up/down button located on one of the hearing prosthesis or the computing device communicatively coupled to the hearing prosthesis.

27. The computer-readable media of claim 20, wherein the hearing prosthesis is one of a cochlear implant, an acoustic hearing aid, a bone anchored hearing aid, a direct acoustic stimulation device, or an auditory brain stem implant.

28. The computer-readable media of claim 21, wherein the computing device is further configured to:

after the hearing prosthesis has applied the at least one signal at the one or more changed intensity levels to the recipient of the hearing prosthesis, receive via the graphical user interface, a command to either (i) accept the changed one or more intensity levels or (ii) not to accept the changed one or more intensity levels;

in response to receiving a command to accept the changed one or more intensity levels, save the changed one or more intensity levels to a channel profile for the first channel group; and in response to receiving a command not to accept the changed one or more intensity levels, configure the channels of the first channel group to the intensity levels they were at before the step of changing the one or more intensity levels of the first channel group.

\* \* \* \* \*

UNITED STATES PATENT AND TRADEMARK OFFICE
CERTIFICATE OF CORRECTION

| | | |
|---|---|---|
| PATENT NO. | : 9,272,142 B2 | Page 1 of 1 |
| APPLICATION NO. | : 13/016315 | |
| DATED | : March 1, 2016 | |
| INVENTOR(S) | : Andrew Botros | |

It is certified that error appears in the above-identified patent and that said Letters Patent is hereby corrected as shown below:

In the claims:

In Col. 24, lines 27-28, delete "changing" and insert --change-- therewith.

In Col. 25, line 52, delete "determining" and insert --determine-- therewith.

Signed and Sealed this
Seventeenth Day of May, 2016

Michelle K. Lee
*Director of the United States Patent and Trademark Office*